United States Patent [19]

Lin et al.

[11] Patent Number: 4,791,120

[45] Date of Patent: Dec. 13, 1988

[54] 4-HETEROPENTACYCLIC-4-[N-(PHENYL-)AMINO] PIPERIDINE DERIVATIVES AND PHARMACEUTICAL COMPOSITIONS AND METHOD EMPLOYING SUCH COMPOUNDS

[75] Inventors: Bor-Sheng Lin, Berkeley Heights; Linas V. Kudzma, North Bergen; H. Kenneth Spencer, Chatham, all of N.J.

[73] Assignee: The BOC Group, Inc., Montvale, N.J.

[21] Appl. No.: 139,899

[22] Filed: Dec. 31, 1987

[51] Int. Cl.[4] .................. A61K 31/445; C07D 405/12; C07D 417/12; C07D 401/12

[52] U.S. Cl. .................................... 514/326; 514/318; 514/329; 514/332; 514/341; 514/342; 546/193; 546/194; 546/201; 546/209; 546/210; 546/211; 546/212; 546/213

[58] Field of Search ............... 514/318, 326, 329, 332, 514/341, 342; 546/193, 194, 201, 209, 210, 211, 212, 213

[56] References Cited

U.S. PATENT DOCUMENTS

| | | | |
|---|---|---|---|
| 3,164,600 | 1/1965 | Janssen | 260/293.4 |
| 3,998,834 | 12/1976 | Janssen et al. | 260/293.68 |
| 4,584,303 | 4/1986 | Huang et al. | 514/326 |

OTHER PUBLICATIONS

McElvain, et al., "Piperidine Derivatives", (1958) JACS, vol. 80 pp. 3915-3923.

*Primary Examiner*—Robert T. Bond

*Attorney, Agent, or Firm*—Chris P. Konkol; Larry R. Cassett

[57] ABSTRACT

Compounds are disclosed of the formula

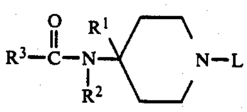

where $R^1$ is an unsubstituted or substituted heterocyclic ring system; $R^2$ is an unsubstituted or substituted phenyl; $R^3$ is a lower alkyl or lower alkoxy, and L is selected from a wide variety of groups.

57 Claims, No Drawings

4-HETEROPENTACYCLIC-4-[N-(PHENYL-)AMINO] PIPERIDINE DERIVATIVES AND PHARMACEUTICAL COMPOSITIONS AND METHOD EMPLOYING SUCH COMPOUNDS

BACKGROUND OF THE INVENTION

The present invention relates to 4-heterocyclic-4-[N-(phenyl)amido]piperidine derivatives and methods and compositions employing such compounds and methods of preparing the same. In particular, this new class of compounds has been found to possess desirable analgesic and anesthetic properties.

A number of patents disclose certain N-phenyl-N-(4-piperidinyl)amides having analgesic activity. For example, some such compounds are disclosed in U.S. Pat. Nos. 3,164,600 and 3,998,834. U.S. Pat. No. 3,164,600 discloses such compounds in which the 4 position of the piperidine ring is substituted by a lower alkyl.

According to the report of S. McElvain et al., JACS, Vol. 80 (1958), changes in the 4-position of certain substituted piperidines generally lead to less or no analgesic activity. For example, McElvain et al. teaches that in going from methyl to butyl, there is no apparent effect on the degree of analgesia, and the 4-phenyl substituent fails to produce any marked effect.

SUMMARY OF THE INVENTION

Compounds of the present invention possess potent analgesic and anesthetic properties. The preferred compounds of the present invention when administered to mammals allow rapid recovery including early regain of muscle coordination. Respiratory depression during use is relatively low compared to commonly known intravenous anesthetics such as fentanyl. Heart rate decrease and arterial pressure decrease are also less. The present compounds are therefore safer, especially for coronary patients.

It has now been found that very desirable agonist properties are provided by compounds of the formula:

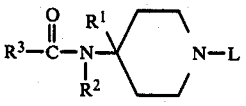

(I)

optically active isomeric forms thereof, and/or pharmaceutically acceptable acid addition salts thereof. In the Formula (I) above, $R^1$ is an unsaturated heterocyclic ring system of 5 cyclic member atoms, including 1 to 4 nitrogen atoms and 0 to 1 sulfur or oxygen atoms, said heterocyclic ring system either unsubstituted or substituted by one or more lower alkyl, lower alkoxy, or lower alkoxy lower alkyl groups, or combinations thereof; $R^2$ is substituted or unsubstituted phenyl in which the substituents are one or more halogen atoms; $R^3$ is a lower alkyl or a lower alkoxy lower alkyl; and L may be a wide variety of groups including lower alkyl, lower alkoxy, thienyl lower alkyl, thiazolyl lower alkyl which can be substituted in the 4-position with a lower alkyl; (4,5-di-hydro-5-oxo-1H-tetrazolyl) lower alkyl which can be substituted in the 4-position with a lower alkyl; pyrazolyl lower alkyl, pyridinyl lower alkyl, oxo phenyl lower alkyl, N-phthalimido lower alkyl, 2,4-(1H,3H)-pyridinedionyl, disubstituted in the 3 position with lower alkyl; and unsubstituted and substituted phenyl lower alkyl in which the substituents are selected from the group consisting of lower alkyl, lower alkoxy, halogen, trihalo lower alkyl or combinations thereof.

A preferred class of compounds within the scope of the present invention are of the formula

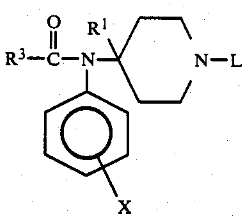

optically active isomeric forms thereof, and/or pharmaceutically acceptable acid addition salts thereof, in which formula: $R^1$ is a substituent selected from the group consisting of oxidiazolyl, imidazolyl, triazolyl, tetrazolyl, and thiazolyl, all of which may be unsubstituted or substituted with lower alkoxy, lower alkoxy lower alkyl, lower alkyl or combinations thereof; X is a halogen or hydrogen group; $R^3$ is lower alkyl or lower alkoxy alkyl of 2–6 carbon atoms; and L is substituted or unsubstituted phenyl lower alkyl, thiazolyl lower alkyl, 4,5-di-hydro-5-oxo-1H-tetrazol-1-yl substituted in the 4-position with a lower alkyl; and thienyl lower alkyl.

DETAILED DESCRIPTION OF THE INVENTION

As noted above, the compounds of the invention have the formula

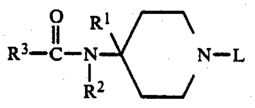

wherein $R^1$ is an unsaturated heterocyclic ring system of 5 cyclic member atoms, including 1 to 4 nitrogen atoms, and 0 to 1 sulfur or oxygen atoms, said heterocyclic ring system either unsubstituted or substituted by lower alkyl, lower alkoxy, lower alkoxy lower alkyl or combinations thereof; $R^2$ is substituted or unsubstituted phenyl; $R^3$ is a lower alkyl or a lower alkoxy lower alkyl group; and L is lower alkyl, lower alkoxy, thienyl lower alkyl, thiazolyl lower alkyl which can be substituted in the 4-position with a lower alkyl; (4,5-di-hydro-5-oxo-1H-tetrazol-1-yl) lower alkyl which can be substituted in the 4-position with a lower alkyl, pyrazolyl lower alkyl, pyridinyl lower alkyl, oxo phenyl lower alkyl, N-pthalimido lower alkyl, 2-4-(1H,3H)-pyridinedionyl, disubstituted in the 3 position with lower alkyl; and unsubstituted and substituted phenyl lower alkyl in which the substituents are selected from the group consisting of lower alkyl, lower alkoxy, halogen, lower haloalkyl (preferably trifluoroalkyl) or combinations thereof. The compounds can be in the form of pharmaceutically acceptable acid addition salts, optically active isomers, and/or cis/trans isomers thereof.

The group $R^1$ in Formula I above is a heterocyclic ring system of 5 cyclic member atoms containing 1 to 4 nitrogen atoms and 0 to 1 oxygen or sulfur atoms. Preferred heterocyclic rings are selected from the group consisting of oxadiazolyl, imidazolyl, triazolyl, thiazolyl, and tetrazolyl. The foregoing rings may be either unsubstituted or substituted, wherein the substituents are selected from the group consisting of lower alkyl, lower alkoxy, lower alkoxy lower alkyl or combinations thereof.

Suitable $R^1$ groups include 1-pyrrolyl, 1,2,4-triazol-4-yl, 1-metylimidazol-2-yl, 1-methyl-1,2,4-triazol-5-yl, 1-methyl-1H-tetrazol-5-yl, 2-methyl-2H-tetrazol-5-yl, methyl ethyl-1,3,4-oxadiazolyl, methoxymethyl-1,3,4-oxadiazolyl, and 4-methyl-thiazol-2-yl.

Preferred L groups are the substituted or unsubstituted phenyl lower alkyl, thienyl lower alkyl, tetrazoly lower alkyl and thiazolyl lower alkyl groups.

The preferred $R^2$ groups are 2-fluorophenyl and phenyl.

The group $R^3$ in Formula I above is a lower alkyl or a lower alkoxy lower alkyl. Example of suitable $R^3$ groups include methoxymethyl, ethoxymethyl, 1-propoxymethyl, 2-propoxymethyl, 1-butoxymethyl, 1-pentoxymethyl, 1-hexoxymethyl, 1-heptoxymethyl, 1-heptoxymethyl, 1-methoxyethyl, 1-ethoxy-1-ethyl, 1-butoxy-1-ethyl, methyl, ethyl, propyl, butyl, pentyl, or hexyl. A preferred $R^3$ group is methyl, ethyl, methoxy or ethoxy.

Suitable L groups include 2-phenylethyl, 1-phenyl-2-propyl, and 2-phenyl-1-propyl, (4,5-di-hydro-5-oxo-1H-tetrazollyl) ethyl substituted in the 4-position with ethyl, thiazolyl ethyl, benzyl, 2-(2-thienyl)ethyl, 2-(3-thienyl) ethyl, 2-(1-pyrazolyl)ethyl, 2-(2-pyridinyl-)ethyl, 2-methyl-butyl, ethyl-1,3,4-oxadiazolyl, 2-(2-pyridinyl)ethyl, 2-ethoxyethyl, 2-oxo-2-phenylethyl, 2-(4-trifluoromethyl) phenylethyl, 2-(4-fluorophenyl-)ethyl, 2-(2-fluorophenyl)ethyl, 2-(N-pthalimido)ethyl), 2-methylbutyl, 2-methylpropyl, 2-(4-methylthiazol-5-yl)ethyl, and 3,3-diethyl-2,4-(1H,3H)-pyridinedion-1-yl) ethyl).

By lower alkyl or lower alkoxy groups, we mean branched or unbranched groups containing from 1 to 6 carbon atoms and preferably 1 to 4 carbon atoms.

The compounds of the invention can exist in the form of the free base or the therapeutically or pharmaceutically acceptable acid addition salts by treatment with an appropriate acid, such as an inorganic acid, e.g., hydrochloric, hydrobromic, sulfuric, nitric, phosphoric acids and the like; or an organic acid such as acetic, trifluoroacetic, propionic, hydroxyacetic, methoxyacetic, benzoic, citric, oxalic, methanesulfonic, ethanesulfonic, benzenesulfonic, toluenesulfonic, succinic, tartaric, and the like acids. Preferred acid addition salts are the chloride and oxalate or citrate. These acid addition salts can be prepared by conventional methods, e.g., by treatment with the appropriate acid.

Compounds of the invention having at least one asymmetric carbon atom can exist in optically active isomeric forms. For example, in compounds in which L is a 1-phenyl-2-propyl group, the carbon adjacent to the piperidinyl nitrogen is an assymetric carbon and such compounds can therefore exist in optical active isomeric (enantiomeric) forms. Such isomeric forms can be isolated from the racemic mixtures by techniques known to those skilled in the art.

The compounds of the invention, prepared as the free base, can be combined with a pharmaceutically acceptable carrer to provide a pharmaceutical composition. Suitable carriers for the free bases include propylene glycol-alcohol-water, isotonic water, sterile water for injection, USP, emulphor TM -alcohol-water, cremophor-EL TM or other carriers known to those skilled in the art.

The compounds of the invention prepared as the pharmaceutically acceptable acid addition salts can also be combined with a pharmaceutically acceptable carrier to provide a pharmaceutical composition. Suitable carriers for the acid addition salts may include an isotonic aqueous solution, or sterile water for injection, USP, alone or in combination with other solubilizing agents such as ethanol, propylene glycol, or other conventional solubilizing agents known to those skilled in the art. Of course, the carrier will vary depending upon the mode of administration desired for the pharmaceutical composition as is conventional in the art. A preferred carrier is an isotonic aqueous solution containing from 0.0001 mg/ml to 0.5 mg/ml of at least one of the compounds of this invention depending upon the pharmacology of the individual compounds being employed in the formulation.

The compounds of the invention can be administered to mammals, e.g., animals or humans, in amounts effective to provide the desired therapeutic effect. The compounds can be administered intravenously, intramuscularly or subcutaneously in the previously described carriers. These compounds may also be administered orally, sublingually, rectally, or transcutaneously with a suitable pharmaceutically acceptable carrier for that mode of administration as is conventional in the art.

As noted above, an effective amount of the compounds of the present invention is employed to obtain the desired therapeutic effect. Since the activity of the compounds and the depth of the desired therapeutic effect vary, the dosage level employed of the compound also varies. The actual dosage administered will be determined by such generally recognized factors as the body weight of the patient or the idiosyncrasies of the particular patient. Thus, the unit dosage for a particular patient (man) can be as low as (0.00005 mg/Kg,) which the practitioner may titrate to the desired effect.

The compounds of the present invention can be prepared beginning with known piperidones as shown below:

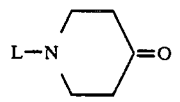

For example, the compound 1-phenylethyl-4-piperidone can be prepared according to the procedure published by A. H. Becket, A. F. Casey and G. Kirk, *J. Med Pharm. Chem.*, Vol. 1, 37 (1959). The compound 1-benzyl-4-piperidone can be prepared in an analogous manner by the procedures described by C. R. Ganellin and R. G. Spickch, *J. Med. Chem.*, Vol. 8, 619 (1965) or P. M. Carabateas and L. Grumbach, *J. Med. Pharm. Chem.*, Vol. 5, 913(1962). Compounds with other L groups can be prepared as disclosed in U.S. Pat. No. 4,584,303 and Ser. No. 07/009,857 filed on Feb. 2, 1987 both incorporated herein by reference.

In one example of a process of the invention, L-piperidone may be reacted with phenyl amine and the resulting Schiff base may be further reacted with, for example, a heterocyclic lithium agent to give a 4-heterocyclic-aminopiperidine or the corresponding substituted heterocyclic compound if a substituted heterocyclic amine is used. The following reaction scheme, wherein $R^1$ represents a heterocyclic group according to the present invention, illustrates such a method:

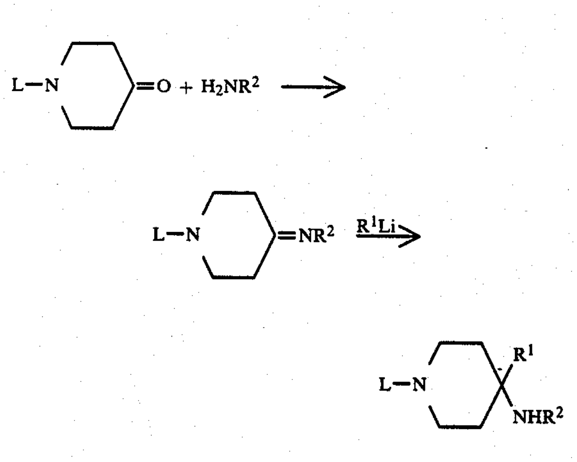

The latter compound can be reacted with the appropriate acid halide, e.g. $R^3(COCl)$ or anhydride $(R^3CO)_2O$ to introduce the appropriate $R^3$—CO— group onto the amino nitrogen as follows.

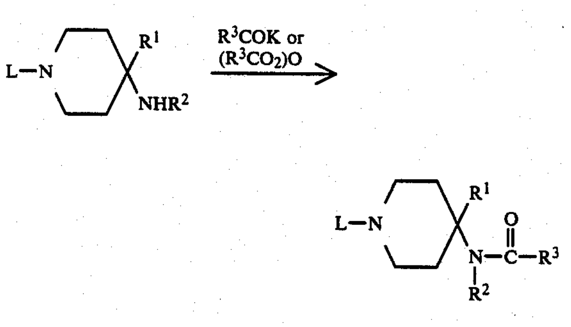

L may originally be phenylmethyl and when L is not phenylmethyl in the final product, one procedure for preparing compounds of the present invention is to subsequently split off the benzyl group and replace it with the desired L group. For example, the compounds of the invention with the exemption of sulfur bearing heterocyclic compounds may be prepared when starting with 1-(2-phenylmethyl)-4-piperidone by the following reaction scheme:

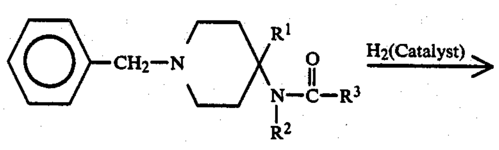

-continued

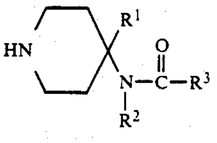

An alternative method of replacing the L group involves employing alpha-chloro-ethylchloroformate to accomplish debenzylation followed by methanolysis.

The appropriate L group can then be introduced by reacting the latter compound with an appropriately reactive molecule LX wherein X is, for example, halogen such as chlorine, bromine or iodine, e.g., as illustrated below

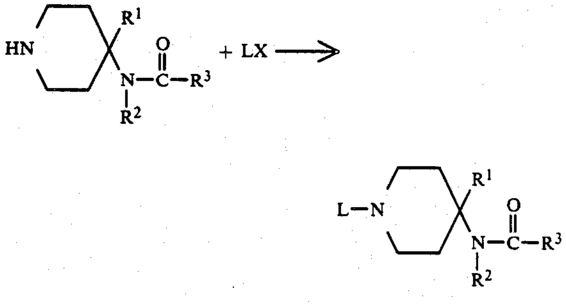

The reaction of LX can be conducted in an inert organic solvent such as, for example, N,N-dimethylformamide (DMF) or acetonitrile in the presence of an appropriate base such as alkali metal carbonate.

Compounds of the invention may also be prepared via a nitrile intermediate by the following reaction scheme:

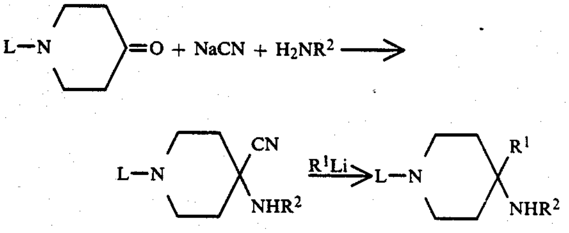

The remaining steps may proceed as shown above.

Another route to the compounds of the present invention with the exception of compounds where the heterocyclic $R_1$ is a thiazolyl, imidiazole, or triazolyl group, is via a functional transformation of a 4-cyano substituent on the piperidine ring. Beginning with the 4-cyano intermediate, the addition of an azide salt results in a functional transformation to a 4-heterocyclic compound. By appropriate reaction, either a tetrazolyl or an oxadiazolyl group may be obtained and the R, R' and L groups may be selected. The reaction scheme may be shown as follows.

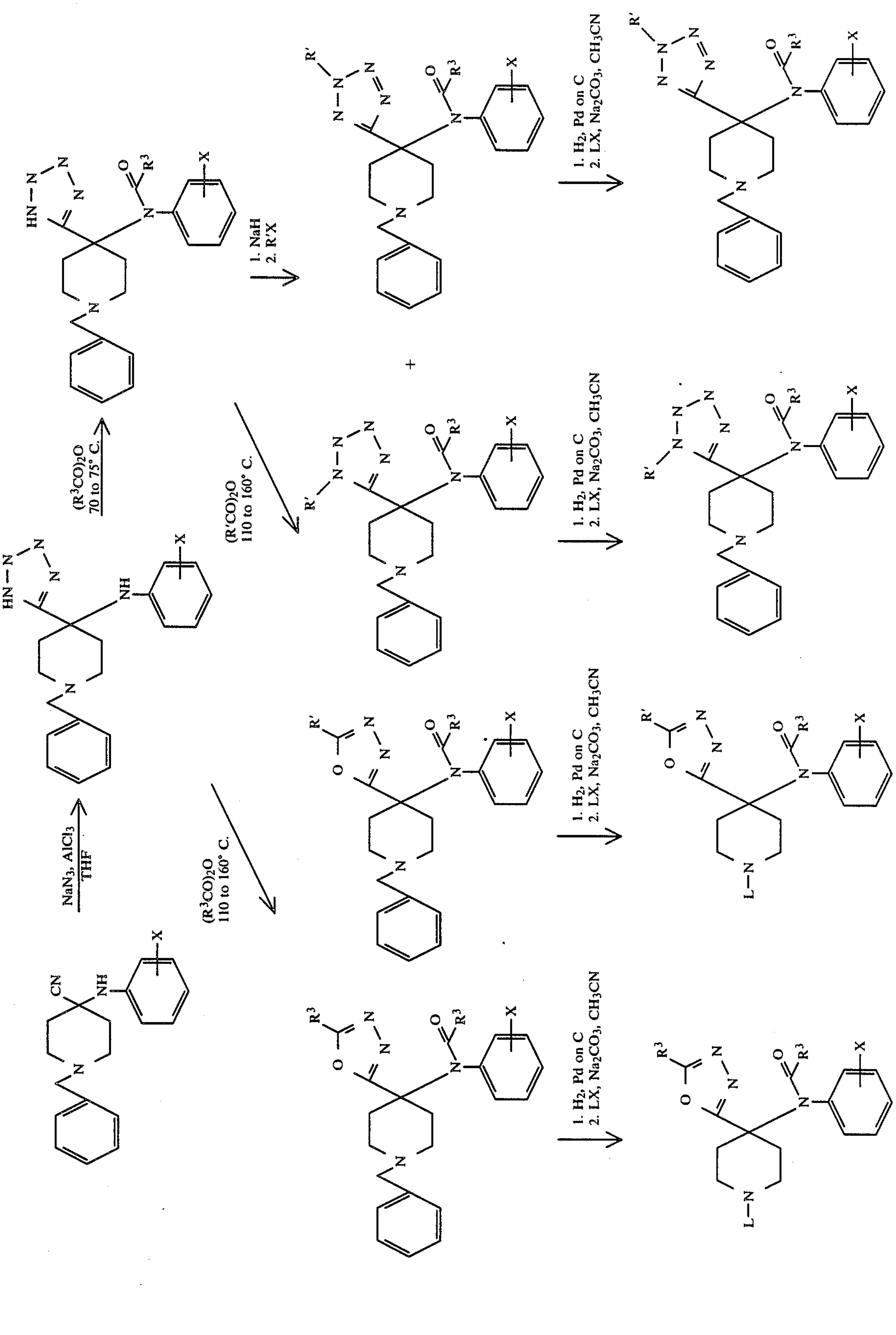
NaN3, AlCl3
THF
(R3CO)2O
70 to 75° C.
1. NaH
2. R'X
+
(R'CO)2O
110 to 160° C.
(R3CO)2O
110 to 160° C.
1. H2, Pd on C
2. LX, Na2CO3, CH3CN
1. H2, Pd on C
2. LX, Na2CO3, CH3CN
1. H2, Pd on C
2. LX, Na2CO3, CH3CN
1. H2, Pd on C
2. LX, Na2CO3, CH3CN wherein in the above reaction scheme L, $R^3$ and X may be as defined above and R' may be selected from lower alkyl, lower alkoxy, or lower alkoxy lower alkyl.

The following examples are presented for the purposes of demonstrating, but not limiting the compounds or compositions of this invention.

EXAMPLE 1

In a well ventilated hood a solution of potassium cyanide (110.5 gms, 1.69 mol) in 680 mls of deionized water was stirred at room temperature (RT). To this solution was added aniline (157.6 gms, 1.69 mol) in 320 mls of methanol. The resulting solution was cooled in an ice/water bath and 12N HCl (140 mls, 1.68 mol) was added dropwise with cooling (Caution HCN). N-benzyl-4-piperidone (320 gms, 1.69 mol) was slowly added with cooling followed by warming reaction mixture to RT. The reaction mixture was stirred at RT for 8 days. When stirring was stopped the reaction mixture separated to two layers. The top aqueous methanol layer was decanted to leave a gummy solid. 200 mls of isopropanol was added to the gummy residue and the mixture was vigorously stirred for 45 minutes. A finely divided solid was formed. This solid was filtered, washed with isopropanol and dried in an over (50° C.) to give 288.2 gms (58.5%) of the desired alpha-amino nitrile as a white powder.

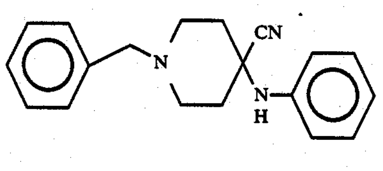

EXAMPLE 2

1-benzyl-4-(4-methyl-thiazol-2-yl)-4-(N-phenyl)piperidine

A solution of 2.5M butyllithium in hexane (103 mls, 257.5 mmol, Aldrich) was added to 150 mls of dry THF under argon and the solution was cooled to −78° C. 4-Methylthiazole (25 mls, 274 mmol, Aldrich 98%) was added to the cold butyllithium solution dropwise via syringe. The solution turned a deep orange and after 5 min. at −78° C. a solution of nitrile (38.54 gms, 132 mmol) prepared in Example 1 dissolved in 350 mls of THF was added rapidly via cannula. The reaction was stirred at −78° C. for 5 min. followed by warming to 0° C. in a water/ice bath. The reaction was quenched at 0° C. by slow dropwise addition of 50 mls of water and stirred for 0.5 hrs. The organic layer was separated, dried over $Na_2SO_4$ and concentrated to give the crude diamine as a dark oil. The oil passed through a column of silica 60 (230–400 mesh) eluting with 1:2 EtOAc/Hex and the resulting pale yellow oil crystallized from hot hexane to give 40.4 gms (84%) of pure diamine.

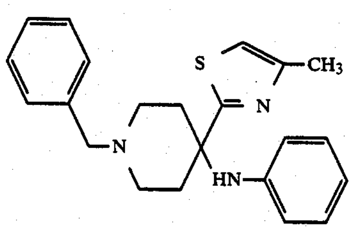

NMR: 7.50–6.40 (m, 11H), 4.25 (br s, 1H), 3.50(s, 2H), 2.45 (s, 3H), 2.90–1.90 (complex, 8H).

EXAMPLE 3

1-benzyl-4-(4-methyl-thiazol-2-yl)-4-(N-phenylpropionamido))piperidine

The diamine (6.97 gms, 19.17 mmol) of Example 2 was dissolved in 150 mls. of dry chloroform and an excess of propionyl chloride (10 mls) was added. The reaction mixture has heated at reflux for 5 days, after which no starting diamine could be detected by TLC. The reaction was cooled and added dropwise to a cold (0° C.) solution of KOH (25 gms) in 500 mls of water and stirred for 2 hrs. The organic layer was separated, dried over $Na_2SO_4$ and concentrated in vacuo to give the desired amide as an amber glass (7.63 gms, 95%).

NMR: 7.50 (s, 5H), 7.35 (s, 5H), 6.85 (s, 1H), 3.40 (s, 2H), 2.85–1.50 (complex, 10H), 2.40 (s, 3H), 0.80 (t, 3H).

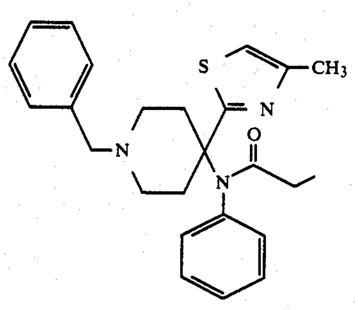

EXAMPLE 4

The amide (9.78 gms, 22.35 mmol) of Example 3 was dissolved in 250 mls of 1,2-dichloroethane and cooled to 0° C. in an ice bath followed by addition of 1-chloroethyl chloroformate (3.53 gms, 24.69 mmol). The solution was warmed to RT and heated to reflux. After 2.5 hrs at reflux the dichloromethane was stripped off in vacuo and the orange residue was redissolved in 200 mls of methanol. The methanol solution was refluxed for 5 hrs, cooled and concentrated in vacuo. The residue was taken up in 400 mls 0.5N HCl and extracted twice with 200 ml portions of ethyl ether. The aqueous layer was basified with 25% aqueous NaOH and extracted with chloroform. The chloroform layer was separated, dried over $Na_2SO_4$ and concentrated to give nor-compound (7.48 gms, 96%) as an oil.

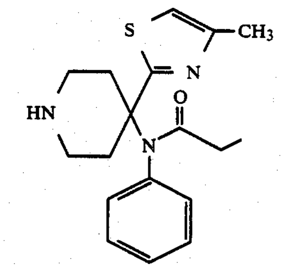

EXAMPLE 5

The nor-compound (1.06 gms, 3.22 mmol) of Example 4 was dissolved in 40 mls of acetonitrile. The solution was stirred and $K_2CO_3$ (1.8 gms) and phenethyl bromide (0.90 gms, 4.86 mmol) were added. The reaction was heated at reflux for 2 days after which the reaction was cooled filtered and concentrated in vacuo. The residue was chromatographed on silica 60 (230-400 mesh) eluting with 1:1 EtOAc/Hex to give compound as a pale yellow oil (1.33 gms, 95%).

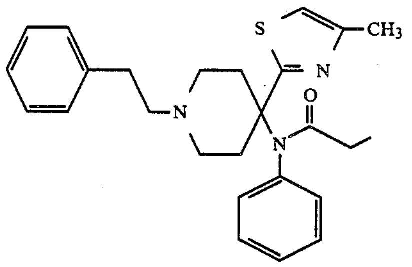

EXAMPLE 6

1-[2-(1H-pyrazol-1-yl)ethyl]-4-(4-methyl-thiazol-2-yl)-4-(N-phenylpropionamido)piperidine The nor-compound (1.06 gms, 3.2 mmol) of Example 4 was dissolved in 45 mls of acetonitrile. The solution was stirred and $K_2CO_3$ (1.35 gms) and 2-(1H-pyrazol-1-yl)ethyl tosylate (0.93 gms, 3.4 mmol) were added. The reaction was heated at reflux for 3 days after which the reaction was cooled filtered and concentrated in vacuo. The residue was chromatographed on silica 60 (230-400 mesh) eluting with 5% methanol in ethyl acetate to give the desired product as an amber oil (1.21 gms, 92%)

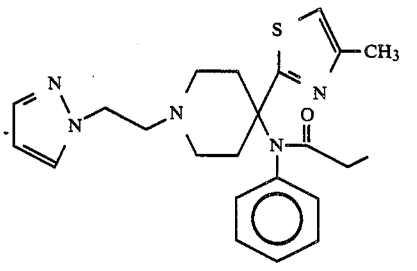

%CHN Analysis of oxalate salt mp = 185°-87° C.

Calc.: %C(58.46), %H(6.08), %N(13.64); Found: 58.19, 6.05, 13.46.

NMR: 7.35 (s, 5H), 6.90 (s, 1H), 6.25 (m, 1H), 4.25 (m, 2H), 2.90-2.10 (complex, 13H), 1.90 (q, 2H), 0.90 (t, 3H).

EXAMPLE 7

1-benzyl-4-(1-methyl-1,2,4-triazol-5-yl)-4-anilino-piperidine

A 500 ml r.b. flask was charged with N-benzylpiperidone (22.72 g, 120 mmol), aniline (11.17 g, 120 mmol), p-toluenesulfonic acid (200 mg) and toluene (250 ml). The mixture was refluxed for 3 hours while separating water through a Dean-Stark trap. The resulting reddish brown solution was cooled to 0° C.

A 1000 ml r.b. flask was charged with 1-methyl-1,2,4-triazole (13.28 g, 160 mmol) and dry THF (400 ml). To this THF solution at −78° C. under $N_2$, n-BuLi (100 ml, 1.6M in Hex) was added. The resulting milky mixture was kept stirring at −78° C. for 2 hours. To this lithio mixture at −78° C., the above toluene solution was added through a needle. After the addition, the resulting mixture was stirred at −78° C. for 30 minutes, gradually warmed up to room temperature and stirred at room temperature for 30 minutes. The reaction was quenched with $H_2O$ (300 ml). The organic layer was separated, dried over $Na_2SO_4$ and concentrated in vacuo. The resulting residue was chromatographed to give the product (20.53 g, 59 mmol) as an amber viscous oil: IR (neat) 3400 cm$^{-1}$; NMR (60 MHz, $CDCl_3$) δ3.53 (s, 2H, benzyl $CH_2$), 3.93 (s, 3H, triazolyl $CH_3$), 6.2 to 7.5 (m's, 10H, phenyl H's), 7.86 (s, 1H, triazolyl H).

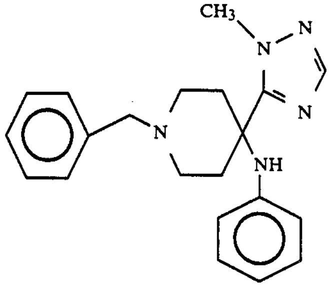

EXAMPLE 8

1-benzyl-4-(1-methyl-1,2,4-triazol-5-yl)-4-(N-phenylpropionamido)piperidine

A mixture of 1-benzyl-4-(1-methyl-1,2,4-triazol-5-yl)-4-anilinopiperidine (11.45 g, 33 mmol) and propionic anhydride (40 ml) was stirred at 140° C. for 70 hrs. It was then concentrated in vacuo. The crude was dissolved $CH_2Cl_2$, washed with 5% $Na_2CO_3$, dried over $Na_2SO_4$ and concentrated in vacuo. The resulting residue was chromatographed ($SiO_2$ EtOAc) to yield the product (8.5 g, 21 mmol); as an amber viscous oil: IR (neat) 1660 cm$^{-1}$; NMR (60 MHZ, $CDCl_3$) δ0.86 (t, 3H, $\underline{CH_3}CH_2CON$), 1.5-3.0 (complex, 10H), 3.35 (s, 2H, benzyl $CH_2$), 4.23 (s, 3H, triazolyl $CH_3$), 7.23 and 7.40 (2bs, 10H, phenyl H's), 7.83 (s, 1H, triazolyl H).

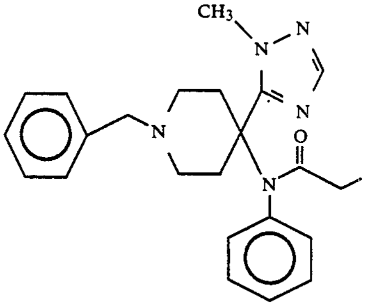

EXAMPLE 9

1-benzyl-4-(1H-tetrazol-5-yl)-4-anilinopiperidine

Sodium azide (5.85 g, 90 mmol) and 1-benzyl-4-cyano-4-anilinopiperidine (2.91 g, 10 mmol) were added slowly to a solution of $AlCl_3$ (2.67 g, 20 mmole) in dry THF (100 ml). The resulting mixture was refluxed overnight. The reaction was quenched with water (50 ml). After separating the THF layer, the aqueous layer was extracted with additional THF (4×50 ml). The combined THF layers were dried over $MgSO_4$ and concentrated in vacuo. The solid obtained was dissolved in 1N.HCl solution and the pH was adjusted to 6.0 with 1N NaOH solution. The resulting mixture was left overnight and filtered to give the product (1.58 g, 4.7 mmol) as white crystalline solid: mp 205°-206° C. (decomposed); IR (nujol) 3300 $cm^{-1}$; NMR (270 MHz, DMSO-$d_6$) δ2.2 to 2.7 (m, 8H, piperidine $CH_2$), 3.53 (s, 2H, benzyl $CH_2$), 6.35, 6.63 and 7.01 (3m, 5H, anilinophenyl H's), 7.25 (m, 5H, benzylphenyl H's). Anal. Calcd. for $C_{19}H_{22}N_6$: C, 68.24; H, 6.63; N, 25.13. Found: C, 68.79; H, 6.76; N, 24.81.

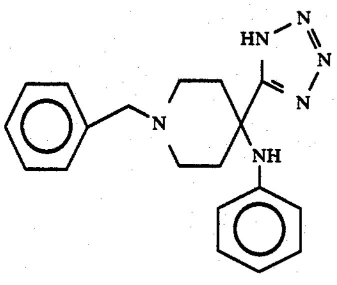

EXAMPLE 10

1-benzyl-4-(1H-tetrazol-5-yl)-4-(2-fluoroanilino)piperidine

To 250 ml of stirring dry THF in a 500 ml r.b. flask at 0° C. under $N_2$, $AlCl_3$ (23.0 g, 172 mmol) was added in small portions. Subsequently, $NaN_3$ (47.4 g, 729 mmol) and 1-benzyl-4-cyano-4-(2-fluoroanilino)piperidine (21.8 g, 70 mmol) were added. The resulting mixture was refluxed for 20 hours. It was cooled to room temperature and poured onto stirring water (300 ml). The THF layer was separated and the aqueous layer was extracted with additional THF (3×500 ml). The combined THF layers were dried over $MgSO_4$ and filtered. The filtrate was kept at 0° C. for 15 hours. After a filtration, the desired compound (17.1 g, 49 mmol) as white powder was obtained: m.p. 195°-198° C.; IR (nujol) 3360 $cm^{-1}$; NMR (270 MHz, DMSO-$d_6$) δ 2.29, 2.46 and 2.67 (3m, 8H, piperidine $CH_2$'s), 3.53 (s, 2H, benzyl $CH_2$), 6.12, 6.61, 6.72 and 6.98 (4m, 4H, anilinophenyl) H's), 7.2-7.4 (m, 5H, benzylphenyl H's). Anal. Calcd. for $C_{19}H_{21}FN_6$: C, 64.75; H, 6.01; N, 23.85. Found: C, 64.52; H, 5.94; N, 23.56.

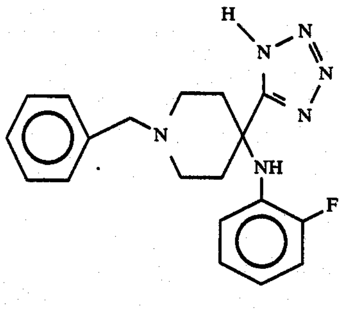

EXAMPLE 11

1-benzyl-4-(1H-tetrazol-5-yl)-4-(N-phenylpropionamido)piperidinium propionate

A 250 ml r.b. flask was charged with 1-benzyl-4-(1H-tetrazol-5-yl)-4-anilinopiperidine (17.7 g, 53 mmol) and propionic anhydride (95 ml). The resulting mixture was stirred at 70°-75° C. for 6 hours. Then, it was concentrated in vacuo and the crude was chromatographed ($SiO_2$, 5-20% $MeOH/CH_2Cl_2$) to give the desired compound (14.7 g, 32 mmol) as white powder: m.p. 226°-228° C.; R (nujol) 1660 $cm^{-1}$; MR (270 MHz, $CDCl_3$) δ 0.864, (t, 3H, $CH_3CH_2CON$), 1.175 (t, 3H, $CH_3CH_2CO_2H$), 1.883 (q, 2H, $CH_3CH_2CO_2H$), 2.113 (m, 4H), 2.395 (q, 2H, $CH_3CH_2CO_2H$), 2.8-3.1 (m, 4H), 3.464 (s, 2H, benzyl $CH_2$), 7.1 to 7.5 (complex, 10H, phenyl H's). Anal. Calcd. for $C_{22}H_{26}N_6O.C_3H_6O_2$: C, 64.64; H, 6.94; N, 18.09. Found: C, 64.65; H, 7.00; N, 17.89.

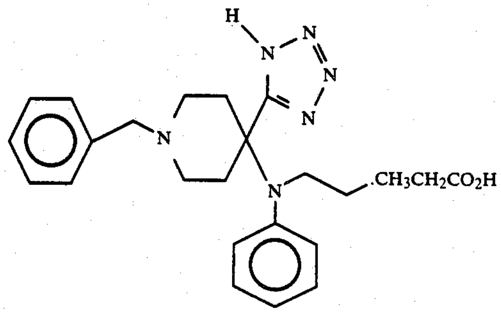

EXAMPLE 12

1-benzyl-4-(1H-tetrazol-5-yl)-4-[N-(2-fluorophenyl)propionamido]piperidine

A 250 ml r.b. flask was charged with 1-benzyl-4-(1H-tetrazol-5-yl)-4-(2-fluoroanilino)piperidine (20.6 g, 58 mmol) and propionic anhydride (100 ml). The resulting mixture was stirred at 70°-75° C. for 24 hours. It was concentrated in vacuo and the residue was chromatographed ($SiO_2$, 5-15% $MeOH/CH_2Cl_2$) to yield the product (8.6 g, 20 mmol) as white powder: m.p. 155°-160° C.; IR (nujol) 1660 $cm^{-1}$; NMR (270 MHz, $CDCl_3$) δ 0.848 (t, 3H, $CH_3CH_2CON$), 1.88 (m, $CH_3CH_2CO$), 3.488 (s, 2H, benzyl $CH_2$), 7.1 to 7.5 (m, 9H, phenyl H's). Anal. Calcd. for $C_{22}H_{25}FN_6O.0.75H_2O$: C, 62.61; H, 6.33; N, 19.91. Found: C, 62.33; H, 6.17; N, 19.88.

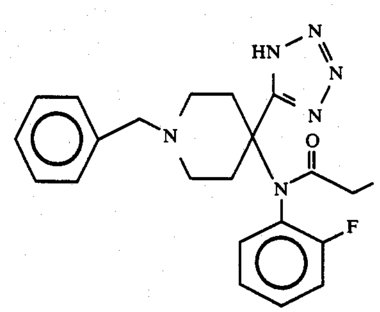

EXAMPLE 13

1-benzyl-4-(methyl-1,3,4-oxadiazolyl)-4-(N-phenylacetamido)piperidine

A 25 ml r.b. flask was charged with 1-benzyl-4-(1H-tetrazol-5-yl)-4-anilinopiperidine (592 mg, 1.77 mmol) and acetic anhydride (10 ml). The resulting mixture was refluxed for 2 hours and concentrated in vacuo. The resulting residue was dissolved in $CH_2Cl_2$ (50 ml), washed with 5% $NaHCO_3$ and $H_2O$. It was dried over $Na_2SO_4$ and concentrated in vacuo. The residue was chromatographed ($SiO_2$, EtOAc) to afford the product (525 mg, 1.34 mmol) as a colorless liquid: IR (neat) 1660

$cm^{-1}$; NMR (60 MHz, $CDCl_3$) δ 1.67 (s, 3H, $CH_3CO$), 2.60 (s, 3H, oxadiazolyl $CH_3$), 3.44 (s, 2H, benzyl $CH_2$), 7.30 and 7.48 (2bs, 10H, phenyl H's). Anal. Calcd. for $C_{23}H_{26}N_4O_2.C_2H_2O_4$: C, 62.49; H, 5.87; N, 11.66. Found: C, 62.56; H, 5.95; N, 11.37.

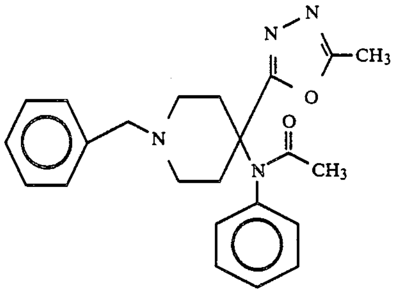

EXAMPLE 14

1-benzyl-4-(ethyl-1,3,4-oxadiazolyl)-4-(N-phenylpropionamido)piperidine

A mixture of 1-benzyl-4-(1H-tetrazol-5-yl)-4-anilinopiperidine (7.45 g, 22 mmol) and propionic anhydride (100 ml) was stirred at 120° for 2 hours ($N_2$ evolution lasted about 20 minutes). The resulting solution was concentrated in vacuo. The crude was dissolved in $CH_2Cl_2$ (400 ml), washed with 5% $NaHCO_3$ (200 ml), dried over $Na_2SO_4$ and concentrated in vacuo. The residue was chromatographed ($SiO_2$, EtOAc/Hex 1:1) to yield the product (8.20 g, 19.6 mmol) as an amber oil: IR (neat) 1670 $cm^{-1}$; NMR (60 MHz, $CDCl_3$) δ 0.89 (t, 3H, $CH_3CH_2CO$), 1.39 (t, 3H, oxadiazolyl $CH_3$), 3.34 (s, benzyl $CH_2$), 7.30 and 7.49 (2bs, 10H, phenyl H's). Anal. Calcd. for $C_{25}H_{30}N_4O_2.C_2H_2O_4$: C, 63.76; H, 6.34; N, 11.02. Found: C, 63.40; H, 6.26; N, 10.79.

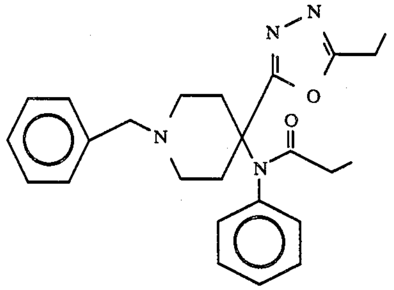

EXAMPLE 15

1-benzyl-4-(methyl-1,3,4-oxadiazolyl)-4-(N-phenylpropionamido)piperidine

A 100 ml r.b. flask was charged with 1-benzyl-4-(1H-tetrazol-5-yl)-4-(N-phenylpropionamido)piperidinium propionate (6.04 g, 13 mmol) and acetic anhydride (50 ml). The resulting mixture was stirred at 110° C. for 2 hours and concentrated in vacuo. The crude was dissolved in $CH_2Cl_2$ (100 ml), washed with 5% $Na_2CO_3$ (100 ml), dried over $Na_2SO_4$ and concentrated in vacuo. The resulting residue was chromatographed ($SiO_2$, EtOAc/Hex 1:1) to give the product (4.20 g, 10.4 mmol) as a viscous oil: NMR (60 MHz, $CDCl_3$) δ 0.90 (t, 3H, $CH_3CH_2CO$), 2.61 (s, 3H, oxadiazolyl $CH_3$), 3.46 (s, 2H, benzyl $CH_2$), 7.33 and 7.52 (2bs, 10H, phenyl H's).

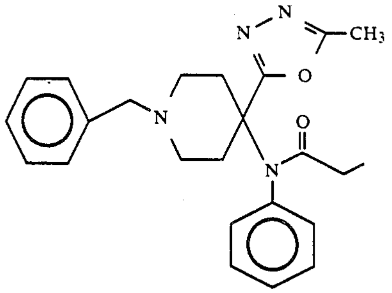

EXAMPLE 16

1-benzyl-4-methoxymethyl-1,3,4-oxadiazolyl)-4-(N-phenylpropionamido)piperidine

To a solution of methoxyacetic acid (4.51 g, 50 mmol) in tripropylamine (80 ml) at 0° C., methoxyacetyl chloride (5.80 g, 53 mmol) was added dropwise. The resulting solution was stirred at 0° C. for 15 minutes. Subsequently, 1-benzyl-4-(1H-tetrazol-5-yl)-4-(N-phenylpropionamido)piperidinium propionate (4.42 g, 9.5 mmol) was added. The whole mixture was stirred at 110° C. for 3 hours and then concentrated in vacuo. The crude was dissolved in ethyl acetate (300 ml), washed with 5% $Na_2CO_3$ (200 ml), dried over $Na_2SO_4$ and concentrated in vacuo. The resulting residue was chromatographed ($SiO_2$, EtOAc/Hex 1:1) to give the product (4.15 g, 9.5 mmol) as an amber oil: NMR (60 MHz, $CDCl_3$) δ 0.89 (t, 3H, $CH_3CH_2CO$), 3.46 (bs, 5H, $CH_3OCH_2$ and $PhCH_2$), 4.70 (s, 2H, $CH_3OCH_2$), 7.27 and 7.47 (2bs, 10H, phenyl H's).

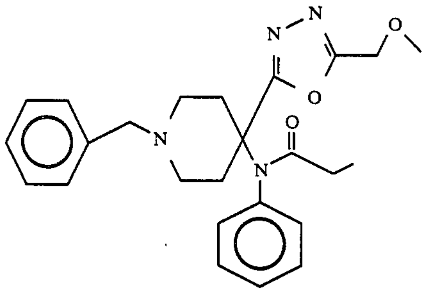

EXAMPLE 17

1-benzyl-4-(ethyl-1,3,4-oxadiazolyl)-4-[N-(2-fluorophenyl)propionamido)piperidine A 250 r.b. flask was charged with 1-benzyl-4-(1H-tetrazol-5-yl)-4-(2-fluoroanilino)piperidine (12.0 g, 34 mmol) and propionic anhydride (80 ml). The resulting mixture was stirred at 160° C. for 48 hours and then concentrated in vacuo. The crude was dissolved in $CH_2Cl_2$ (200 ml), washed with 5% $Na_2CO_3$ (100 ml), dried over $Na_2SO_4$ and concentrated in vacuo. The resulting residue was chromatographed ($SiO_2$, EtOAc/-Hex 2:1) to yield the product (5.75 g, 13 mmol) as a viscous oil: NMR (60 MHz, $CDCl_3$) δ 0.93 (t, 3H, $CH_3CH_2CO$), 1.40 (t, 3H, oxadiazolyl $CH_3$), 3.50 (s, 2H, benzyl $CH_2$), 7.1–7.8 (m, 9H, phenyl H's).

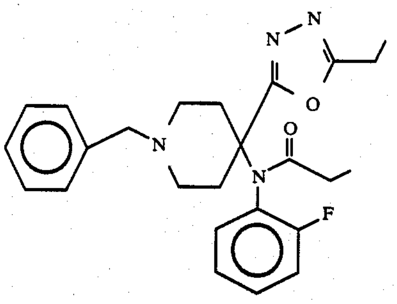

EXAMPLE 18

1-benzyl-4-(1 and 2 methyl-1H-tetrazol-5-yl-4-(N-phenylpropionamido)-piperidines To a stirring mixture of 1-benzyl-4-(1H-tetrazol-5-yl)-4-(N-phenylpropionamido)piperidinium propionate (18.9 g, 40.7 mmol) and DMF (120 ml), NaH (2.4 g,m 100 mmol) was added. The mixture was stirred at room temperature for 30 minutes. To the resulting brown solution, iodomethane (15 g, 106 mmol) was added slowly. It was stirred for 30 minutes and poured onto $H_2O$ (400 ml). The mixture was extracted with $CH_2Cl_2$ (2×250 ml). The $CH_2Cl_2$ solution was washed with $H_2O$ (4×400 ml), dried over $Na_2SO_4$ and concentrated in vacuo. The resulting residue was chromatographed ($SiO_2$, 1% MeOH/$CH_2Cl_2$) to give 1-benzyl-4-(1-methyl-1H-tetrazol-5-yl)-4-(N-phenylpropionamido)piperidine (4.58 g, 11.3 mmol) as a colorless viscous oil: IR (neat) 1660 $cm^{-1}$; NMR (270 MHZ, $CDCl_3$) δ 0.834, (t, 3H, $\underline{CH_3}CH_2CO$), 1.789 (q, 2H, $CH_3\underline{CH_2}$), 3.334 (s, 2H, ph$CH_2$), 4.435 (s, 3H, tetrazolyl $CH_3$), 7.15 to 7.47 (m's, 10H, phenyl H's), and 1-benzyl-4-(2-methyl-2H-tetrazol-5-yl)-4-(N-phenyl)propionamido)piperidine (2.75 g, 6.8 mmol) as a viscous oil: IR (neat) 1660 $cm^{-1}$; NMR (270 MHz, $CDCl_3$) δ 0.830 (t, 3H, $\underline{CH_3}CH_2CO$), 1.810 (q, 2H, $CH_3\underline{CH_2}$), 3.402 (s, 2H, ph$CH_2$), 4.369 (s, 3H, tetrazolyl $CH_3$), 7.20 to 7.54 (3m's, 10H, phenyl H's).

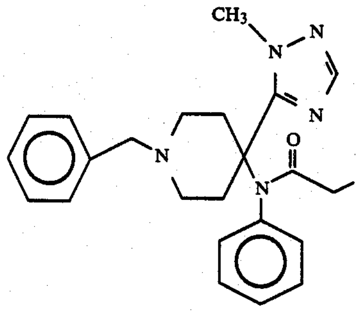

and

-continued

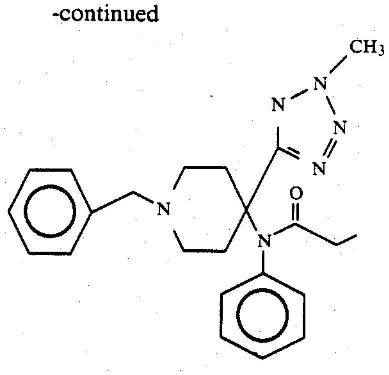

EXAMPLE 19

4-(ethyl-1,3,4-oxadiazolyl)-4-(N-phenylpropionamido)-piperidine

A mixture of 1-benzyl-4-(ethyl-1,3,4-oxadiazolyl)-4-(N-phenylpropionamido)piperidine (8.20 g, 19.6 mmol) and 10% palladium on charcoal (2.0 g) in methanol (100 ml) was reacted with hydrogen (50 psi) in a Parr shaker. After 24 hours, the resulting mixture was filtered and the filtrate was concentrated in vacuo. A foamy residue (6.42 g, 19.5 mmol) was obtained. It was used for reactions without further purification.

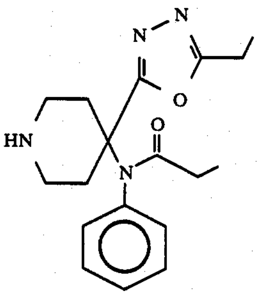

EXAMPLE 20

1-(2-phenylethyl)-4-(ethyl-1,3,4-oxadiazolyl)-4-(N-phenylpropionamido)piperidine A mixture of 4-(ethyl-1,3,4-oxadiazolyl)-4-(N-phenylpropionamido)piperidine (900 mg, 2.74 mmol), phenethyl bromide (507 mg, 2.74 mmol, NaI (490 mg, 3.3 mmol), $Na_2CO_3$ (2.0 g) in acetonitrile (50 ml) was refluxed for 72 hours. It was filtered and concentrated in vacuo. The residue was treated with $CH_2Cl_2$ (100 ml) and filtered again. The filtrate was concentrated in vacuo and the resulting residue was chromatographed ($SiO_2$, EtOAc/Hex 1:1) to give the product (904 mg, 2.1 mmol) as a colorless oil: IR (neat) 1660 $cm^{-1}$; NMR (60 MHz, $CDCl_3$) δ 0.87 (t, 3H, $\underline{CH_3}CH_2CON$), 1.37 (t, 3H, oxadiazolyl $CH_3$), 1.60–3.15 (m, 16H), 7.23 and 7.50 (2bs, 10H, phenyl H's).

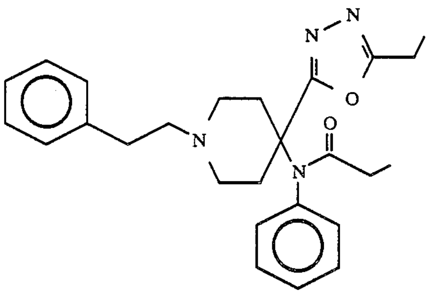

EXAMPLE 21

1-(2-phenethyl)-4-(ethyl-1,3,4-oxadiazolyl)-4-(N-phenylpropionamido)piperidinium oxalate To a solution of 1-(2-phenylethyl)-4-(ethyl-1,3,4-oxadiazolyl)-4-(N-phenylpropionamido)piperidine (417 mg, 0.96 mmol) in ethyl acetate (20 ml), oxalic acid (87 mg, 0.97 mmol) in 2 ml EtOAc) was added dropwise. The resulting mixture was heated to 70° C. and methanol added dropwise until it became a clear solution. The solution was cooled to room temperature on standing for 2 hours. After filtration, the product (408 mg, 0.77 mmol) as a crystalline compound was obtained, mp 159°-161° C. Anal. Calcd. for $C_{26}H_{32}N_4O_2.C_2H_2O_4.\frac{1}{4}$ $H_2O$: C, 63.80; H, 6.60; N, 10.63. Found: C, 63.93; H, 6.65; N, 10.75.

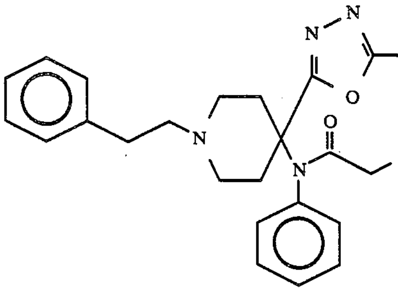

$.C_2H_2O_4$

EXAMPLE 22

1-[2-(2-thienyl)]ethyl-4-(ethyl-1,3,4-oxadiazolyl)-4-(N-phenylpropionamido)piperidine A mixture of 4-(ethyl-1,3,4-oxadiazolyl)-4-(N-phenyl propionamido)piperidine (880 mg, 2.68 mmol), 2-(2-thienyl)ethyl chloride (385 mg, 2.63 mmol), NaI (470 mg, 3.1 mmol) and $Na_2CO_3$ (2.0 g) in acetonitrile (50 ml) was refluxed for 72 hours. It was cooled down to room temperature and filtered. The filtrate was concentrated in vacuo and the residue was treated with $CH_2Cl_2$ (100 ml). The resulting mixture was filtered and the filtrate was concentrated in vacuo. The residue was chromatographed to give the product (940 mg, 2.14 mmol) as an amber oil: IR (neat) 1660 $cm^{-1}$; NMR (60 MHz, $CDCl_3$) $\delta$ 0.88 (t, 3H, $\underline{CH_3}CH_2CO$), 1.39 (t, 3H, oxadiazolyl $CH_3$), 1.60 to 3.20 (m, 16H), 6.70 to 7.40 (m, 3H, thienyl H's) 7.44 (s, 5H, phenyl H's).

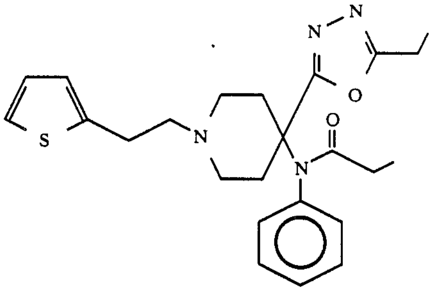

EXAMPLE 23

1-[2-(2-thienyl)ethyl]-4-(ethyl-1,3,4-oxadiazolyl)-4-(N-phenylpropionamido)piperidinium oxalate To a solution of 1-[2-(2-thienyl)ethyl]-4-(ethyl-1,3,4-oxadiazolyl)-4-(N-phenylpropionamido)piperidine (660 mg, 1.50 mmol) in ethyl acetate (20 ml), oxalic acid (136 mg, 1.51 mmol, in 3 ml EtoAc) was added dropwise. The resulting mixture was heated to 70° C. and methanol added dropwise until it became a clear solution. The solution was cooled to room temperature on standing for 2 hours. The precipitate was filtered to afford the product (630 mg, 1.19 mmol) as a white crystalline compound, mp 160°-162° C. Anal. Calcd. for $C_{24}H_{30}N_4O_2S.C_2H_2O_4$: C, 59.07; H, 6.10; H, 10.60 Found: C, 59.08; H, 6.26; N, 10.45.

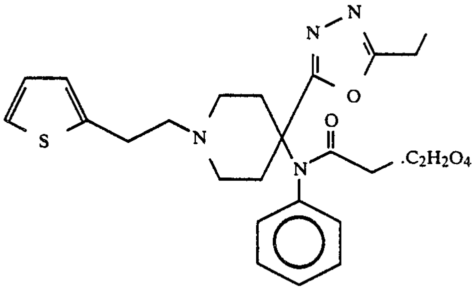

$.C_2H_2O_4$

A number of compounds in accordance with the present invention were tested for their analgesic and reversal properties. Specifically, the acid addition oxalate salts of the compounds tested in accordance with the invention were dissolved in sterile water for injection, USP, to form a solution whose concentration varied from 0.00001 mg/ml to 5 mg/ml. The solution was administered intravenously in a mouse tail vain.

The $ED_{50}$ values were obtained from the mouse hot plate analgesia test (58° C.) described in Domer, Floyd R., *Animal Experiments in Pharmacological Analysis,* Charles C. Thomas, Springfield, 1971, p. 283 ff. The compounds listed in Table 1 below were tested by this procedure and found to have the analgesic activities listed in Tables I, II and III below.

TABLE I

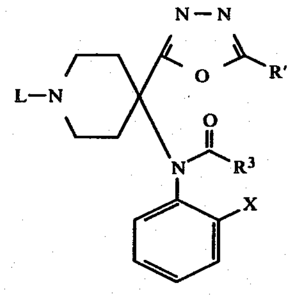

| Compound | L | R' | $R^3$ | X | M.P. (°C.) | $ED_{50}$ mg/kg mouse hot plate |
|---|---|---|---|---|---|---|
| 1-benzyl-4-(methyl-1,3,4-oxadiazolyl)-4-(N—phenylacetamido)piperidinium oxalate | 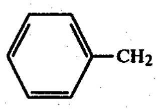 | $CH_3$ | $CH_3$ | H | 198–200 | >5.0 |
| 1-(2-phenylethyl)-4-(methyl-1,3,4-oxadiazolyl)-4-(N—phenylacetamido)piperidinium oxalate | 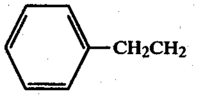 | $CH_3$ | $CH_3$ | H | 219–221 | 0.395 |
| 1-[2-(thienyl)ethyl)-4-(methyl-1,3,4-oxadiazolyl)-4-(N—phenylacetamido)piperidinium oxalate | 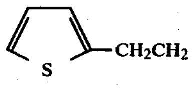 | $CH_3$ | $CH_3$ | H | 237–239 | >1.0 |
| 1-[2-(4-ethyl-4,5-dihydro-5-oxo-1H—tetrazol-1-yl)ethyl]-4-(methyl-1,3,4-oxadiazolyl)-4-(N—phenylacetamido)piperidinium oxalate | 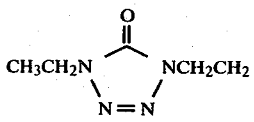 | $CH_3$ | $CH_3$ | H | 174–176 | >5.0 |
| 1-[2-(1-pyrazolyl)ethyl]-4-(methyl-1,3,4-oxadiazolyl)-4-[N—(2-fluorophenyl)acetamido]piperidinium chloride | 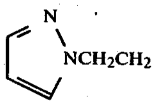 | $CH_3$ | $CH_3$ | F | 131–135 | >5.0 |
| 1-[2-(2-thienyl)ethyl]-4-(methyl-1,3,4-oxadiazolyl)-4-[N—(2-fluorophenyl)acetamido]piperidinium chloride | 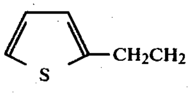 | $CH_3$ | $CH_3$ | F | 155–160 | 0.156 |

TABLE I-continued

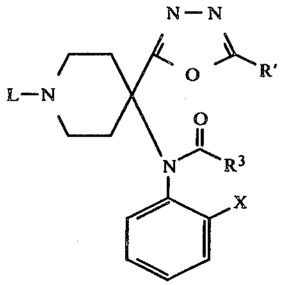

| Compound | L | R' | $R^3$ | X | M.P. (°C.) | $ED_{50}$ mg/kg mouse hot plate |
|---|---|---|---|---|---|---|
| 1-[2-(3-thienyl)ethyl]-4-(methyl-1,3,4-oxadiazolyl)-4-[N—(2-fluorophenyl)acetamido]piperidinium chloride | 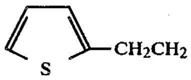 | $CH_3$ | $CH_3$ | F | 143-147 | 0.159 |
| 1-(2-methylbutyl)-4-(methyl-1,3,4-oxadiazolyl)-4-[N—(2-fluorophenyl)acetamido]piperidinium chloride | $CH_3CH_2CHCH_3CH_2$ | $CH_3$ | $CH_3$ | F | 126-128 | 0.458 |
| 1-(2-phenylethyl)-4-(methyl-1,3,4-oxadiazolyl)-4-[N—(2-fluorophenyl)acetamido]piperidinium chloride | 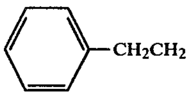 | $CH_3$ | $CH_3$ | F | 150-155 | 0.059 |
| 1-[2-(4-ethyl-4,5-dihydro-5-oxo-1H—tetrazol-1-yl)-ethyl]-4(methyl-1,3,4-oxadiazolyl)-4[N—(2-fluorophenyl)-acetamido]piperidinium chloride | 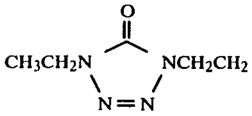 | $CH_3$ | $CH_3$ | F | 133-137 | >5.0 |
| 1-benzyl-4-(ethyl-1,3,4-oxadiazolyl)-4-(N—phenyl-propionamido)piperidinium oxalate | 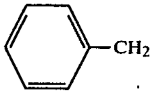 | $CH_3CH_2$ | $CH_3CH_2$ | H | 180-182 | >5.0 |
| 1-(2-phenylethyl)-4-(ethyl-1,3,4-oxadiazolyl)-4-(N—phenyl-propionamido)piperidinium oxalate | 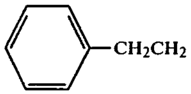 | $CH_3CH_2$ | $CH_3CH_2$ | H | 159-161 | 0.215 |

TABLE I-continued

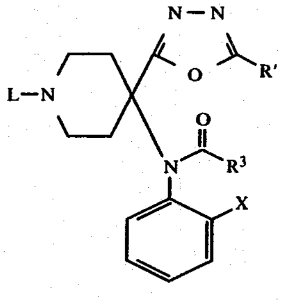

| Compound | L | R′ | $R^3$ | X | M.P. (°C.) | $ED_{50}$ mg/kg mouse hot plate |
|---|---|---|---|---|---|---|
| 1-[2-(2-thienyl)ethyl]-4-(ethyl-1,3,4-oxadiazolyl)-4-(N—phenylpropionamido)piperidinium oxalate | 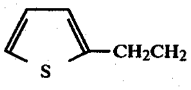 | $CH_3CH_2$ | $CH_3CH_2$ | H | 160–162 | 0.272 |
| 1-[2-(4-ethyl-4,5-dihydro-5-oxo-1H—tetrazol-1-yl)-ethyl]-4-(ethyl-1,3,4-oxadiazolyl)-4-(N—phenyl-propionamido)piperidinium oxalate | 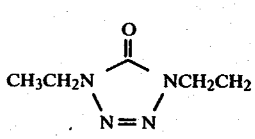 | $CH_3CH_2$ | $CH_3CH_2$ | H | 175–177 | >5.0 |
| 1-[2-(3-thienyl)ethyl]-4-(ethyl-1,3,4-oxadiazolyl)-4-(N—phenylpropionamido)piperidinium oxalate | 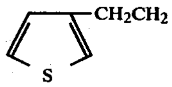 | $CH_3CH_2$ | $CH_3CH_2$ | H | 178–180 | 0.348 |
| 1-[2-(2-pyridinyl)ethyl]-4-(ethyl-1,3,4-oxadiazolyl)-4-(N—phenylpropionamido)piperidinium oxalate | 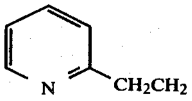 | $CH_3CH_2$ | $CH_3CH_2$ | H | 164–166 | 1.65 |
| 1-(2-ethoxyethyl)-4-(ethyl-1,3,4-oxadiazolyl)-4-(N—phenylpropionamido)piperidinium oxalate | $CH_3CH_2OCH_3CH_2$ | $CH_3CH_2$ | $CH_3CH_2$ | H | 207–210 | >5.0 |
| 1-(2-oxo-2-phenylethyl)-4-(ethyl-1,3,4-oxadiazolyl)-4-(N—phenylpropionamido)piperidinium oxalate | 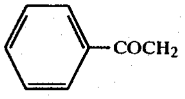 | $CH_3CH_2$ | $CH_3CH_2$ | H | 134–136 | >5.0 |

TABLE I-continued

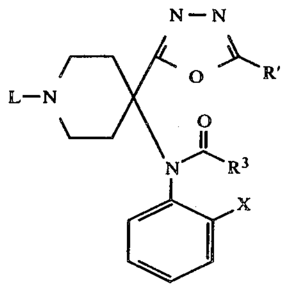

| Compound | L | R' | $R^3$ | X | M.P. (°C.) | $ED_{50}$ mg/kg mouse hot plate |
|---|---|---|---|---|---|---|
| 1-[2-(4-trifluoromethyl)phenylethyl]-4-(ethyl-1,3,4-oxadiazolyl)-4-(N—phenylpropionamido)piperidinium oxalate | 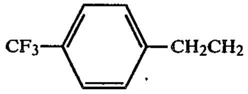 | $CH_3CH_2$ | $CH_3CH_2$ | H | 167-169 | 0.49 |
| 1-[2-(1-pyrazolyl)ethyl]-4-(ethyl-1,3,4-oxadiazolyl)-4-(N—phenylpropionamido)piperidinium oxalate | 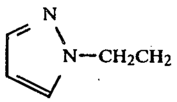 | $CH_3CH_2$ | $CH_3CH_2$ | H | 185-187 | >5.0 |
| 1-(2-phenylethyl)-4-(ethyl-1,3,4-oxadiazolyl)-4-[N—(2-fluorophenyl)propionamido]piperidinium chloride | 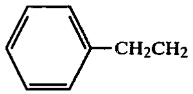 | $CH_3CH_2$ | $CH_3CH_2$ | F | 95-102 | 0.018 |
| 1-[2-(2-thienyl)ethyl]-4-(ethyl-1,3,4-oxadiazolyl)-4-[N—(2-fluorophenyl)propionamido]piperidinium chloride | 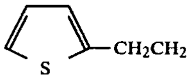 | $CH_3CH_2$ | $CH_3CH_2$ | F | 85-90 | 0.063 |
| 1-[2-(3-thienyl)ethyl]-4-(ethyl-1,3,4-oxadiazolyl)-4-[N—(2-fluorophenyl)propionamido]piperidinium chloride | 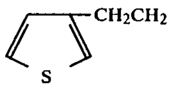 | $CH_3CH_2$ | $CH_3CH_2$ | F | 70-75 | 0.171 |
| 1-[2-(2-pyridinyl)ethyl]-4-(ethyl-1,3.4-oxadiazolyl)-4-[N—(2-fluorophenyl)propionamido)piperidinium chloride | 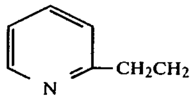 | $CH_3CH_2$ | $CH_3CH_2$ | F | 131-139 | >5.0 |

TABLE I-continued

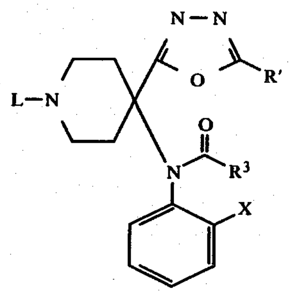

| Compound | L | R' | $R^3$ | X | M.P. (°C.) | $ED_{50}$ mg/kg mouse hot plate |
|---|---|---|---|---|---|---|
| 1-(2-phenylethyl)-4-(methyl-1,3,4-oxadiazolyl)-4-(N—phenylpropionamido)piperidinium oxalate | 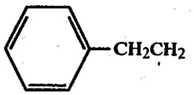 | $CH_3$ | $CH_3CH_2$ | H | 205–207 | 0.027 |
| 1-[2-(2-thienyl)ethyl]-4-(methyl-1,3,4-oxadiazolyl)-4-(N—phenylpropionamido)piperidinium oxalate | 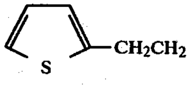 | $CH_3$ | $CH_3CH_2$ | H | 202–203 | 0.10 |
| 1-[2-(3-thienyl)ethyl]-4-(methyl-1,3,4-oxadiazolyl)-4-(N—phenylpropionamido)piperidinium oxalate | 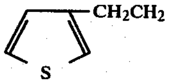 | $CH_3$ | $CH_3CH_2$ | H | 198–200 | 0.016 |
| 1-[2-(4-fluorophenyl)ethyl]-4-(methyl-1,3,4-oxadiazolyl)-4-(N—phenylpropionamido)piperidinium oxalate | 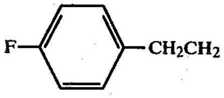 | $CH_3$ | $CH_3CH_2$ | H | 200–202 | 0.242 |
| 1-[2-(4-trifluorophenyl)ethyl]-4-(methyl-1,3,4-oxadiazol-yl)-4-(N—phenylpropionamido)piperidinium oxalate | 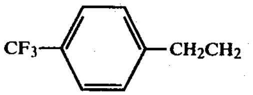 | $CH_3$ | $CH_3CH_2$ | H | 130–132 | 0.309 |
| 1-[2-(2-pyridinyl)ethyl]-4-(methyl-1,3,4-oxadiazolyl)-4-(N—phenylpropionamido)piperidinium oxalate | 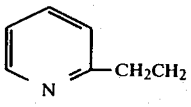 | $CH_3$ | $CH_3CH_2$ | H | 176–177 | >1.0 |

TABLE I-continued

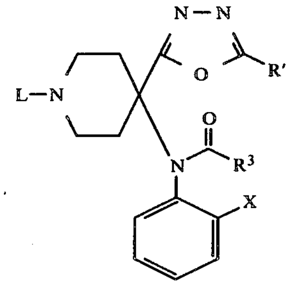

| Compound | L | R' | $R^3$ | X | M.P. (°C.) | $ED_{50}$ mg/kg mouse hot plate |
|---|---|---|---|---|---|---|
| 1-[2-(2-fluorophenyl)ethyl]-4-(methyl-1,3,4-oxadiazolyl)-4-(N—phenylpropionamido)piperidinium oxalate | 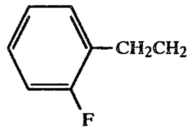 | $CH_3$ | $CH_3CH_2$ | H | 196-197 | 0.0049 |
| 1-[2-(4-ethyl-4,5-dihydro-5-oxy-1H—tetrazol-1-yl)ethyl]-4-(methyl-1,3,4-oxadiazolyl)-4-(N—phenylpropionamido)piperidinium oxalate | 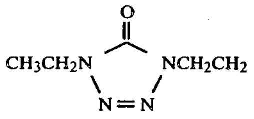 | $CH_3$ | $CH_3CH_2$ | H | 162-165 | 0.772 |
| 1-[2-(1-pyrazolyl)ethyl]-4-(methyl-1,3,4-oxadiazolyl)-4-(N—phenylpropionamido)piperidinium oxalate | 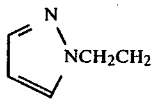 | $CH_3$ | $CH_3CH_2$ | H | 183-184 | 0.063 |
| 1-[2-(N—phthalimido)ethyl]-4-(methyl-1,3,4-oxadiazolyl)-4-(N—phenylpropionamido)piperidinium oxalate | 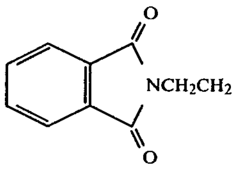 | $CH_3$ | $CH_3CH_2$ | H | 164-167 | >5.0 |
| 1-(2-phenylethyl)-4-(methyl-1,3,4-oxadiazolyl)-4-[N—(2-fluorophenyl)propionamido]piperidinium chloride | 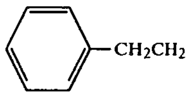 | $CH_3$ | $CH_3CH_2$ | F | 133-137 | 0.016 |

TABLE I-continued

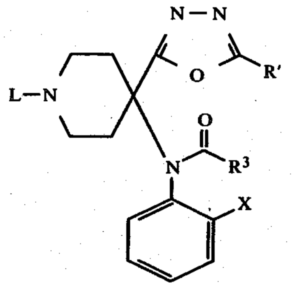

| Compound | L | R' | $R^3$ | X | M.P. (°C.) | $ED_{50}$ mg/kg mouse hot plate |
|---|---|---|---|---|---|---|
| 1-[2-(2-pyridinyl)ethyl]-4-(propyl-1,3,4-oxadiazolyl)-4-[N—(2-fluorophenyl)propionamido]piperidinium chloride | 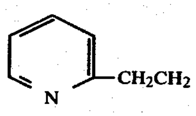 | $CH_3$ | $CH_3CH_2$ | F | 161-163 | 0.525 |
| 1-(2-methylbutyl)-4-(methoxymethyl-1,3,4-oxadiazolyl)-4-(N—phenylpropionamido)piperidinium oxalate | $CH_3CH_2CHCH_3CH_2$ | $CH_3$ | $CH_3CH_2$ | H | 182-183 | 0.484 |
| 1-[2-(2-thienyl)ethyl]-4-(methyl-1,3,4-oxadiazolyl)-4-[N—(2-fluorophenyl)propionamido]piperidinium chloride | 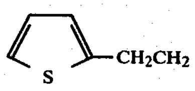 | $CH_3$ | $CH_3CH_2$ | F | 120-125 | 0.017 |
| 1-[2-(1-pyrazolyl)ethyl]-4-(methyl-1,3,4-oxadiazolyl)-4-[N—(2-fluorophenyl)propionamido]piperidinium chloride | 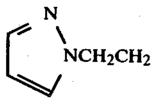 | $CH_3$ | $CH_3CH_2$ | F | 120-123 | >5.0 |
| 1-(2-phenylethyl)-4-(propyl-1,3,4-oxadiazolyl)-4-(N—phenylpropionamido)piperidinium chloride | 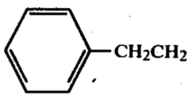 | $CH_3CH_2CH_2$ | $CH_3CH_2$ | H | 110-114 | 0.0017 |
| 1-[2-(2-thienyl)ethyl]-4-(propyl-1,3,4-oxadiazolyl)-4-(N—phenylpropionamido)piperidinium chloride | 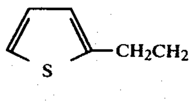 | $CH_3CH_2CH_2$ | $CH_3CH_2$ | H | 105-110 | 0.0014 |

TABLE I-continued

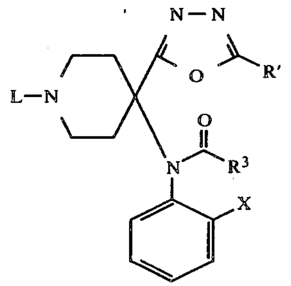

| Compound | L | R' | $R^3$ | X | M.P. (°C.) | $ED_{50}$ mg/kg mouse hot plate |
|---|---|---|---|---|---|---|
| 1-[2-(4-fluorophenyl)ethyl]-4-(propyl-1,3,4-oxadiazolyl)-4-(N—phenylpropionamido)piperidinium chloride | 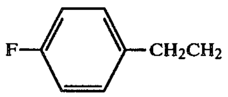 | $CH_3CH_2CH_2$ | $CH_3CH_2$ | H | 111-115 | 0.0082 |
| 1-[2-(1-pyrazolyl)ethyl]-4-(propyl-1,3,4-oxadiazolyl)-4-(N—phenylpropionamido)piperidinium oxalate | 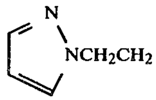 | $CH_3CH_2CH_2$ | $CH_3CH_2$ | H | 112-115 | 0.276 |
| 1-[2-(4-trifluorophenyl)ethyl]-4-(propyl-1,3,4-oxadiazolyl)-4-(N—phenylpropionamido)piperidinium chloride | 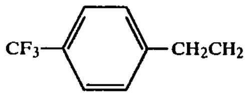 | $CH_3CH_2CH_2$ | $CH_3CH_2$ | H | 107-111 | 0.08 |
| 1-[2-(2-pyridinyl)ethyl]-4-(propyl-1,3,4-oxadiazolyl)-4-(N—phenylpropionamido)piperidinium oxalate | 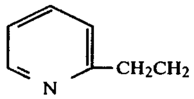 | $CH_3CH_2CH_2$ | $CH_3CH_2$ | H | 150-155 | >1.0 |
| 1-(2-methylbutyl)-4-(propyl-1,3,4-oxadiazolyl)-4-[N—(2-fluorophenyl)propionamido]piperidinium chloride | $CH_3CH_2CHCH_3CH_2$ | $CH_3CH_2CH_2$ | $CH_3CH_2$ | F | 110-113 | 0.195 |
| 1-[2-(4-ethyl-4,5-dihydro-5-oxy-1H—tetrazol-1-yl)-ethyl]-4-(propyl-1,3,4-oxadiazolyl)-4-[N—(2-fluorophenyl)propionamido]piperidinium chloride | 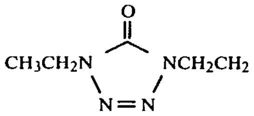 | $CH_3CH_2CH_2$ | $CH_3CH_2$ | F | 119-121 | >1.0 |

TABLE I-continued

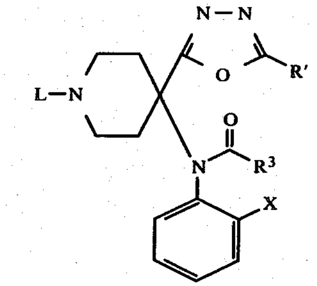

| Compound | L | R' | $R^3$ | X | M.P. (°C.) | $ED_{50}$ mg/kg mouse hot plate |
|---|---|---|---|---|---|---|
| 1-[2-(N—phthalimido)ethyl]-4-(propyl-1,3,4-oxadiazolyl)-4-[N—(2-fluorophenyl)propionamido]piperidinium chloride | 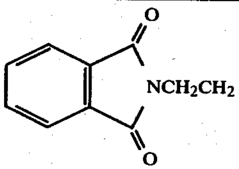 | $CH_3CH_2CH_2CH_2$ | $CH_3CH_2$ | H | 145–150 | >1.0 |
| 1-(2-phenylethyl)-4-(butyl-1,3,4-oxadiazolyl)-4-(N—phenylpropionamido)piperidinium chloride | 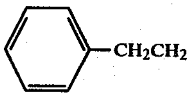 | $CH_3CH_2CH_2CH_2$ | $CH_3CH_2$ | H | 109–110 | 0.0017 |
| 1-[2-(1-pyrazolyl)ethyl]-4-(butyl-1,3,4-oxadiazolyl)-4-(N—phenylpropionamido)piperidinium chloride | 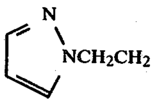 | $CH_3CH_2CH_2CH_2$ | $CH_3CH_2$ | H | 99–103 | >1.0 |
| 1-[2-(4-ethyl-4,5-dihydro-5-oxy-1H—tetrazol-1-yl)-ethyl]-4-(butyl-1,3,4-oxadiazolyl)-4-(N—phenyl-propionamido)piperidinium chloride | 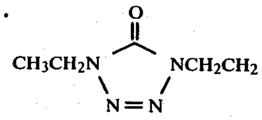 | $CH_3CH_2CH_2CH_2$ | $CH_3CH_2$ | H | 108–110 | 0.149 |
| 1-[2-(N—phthalimido)ethyl]-4-(butyl-1,3,4-oxadiazolyl)-4-(N—phenylpropionamido)piperidinium chloride | 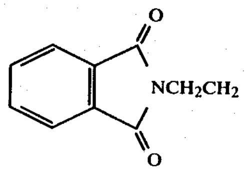 | $CH_3CH_2CH_2CH_2$ | $CH_3CH_2$ | H | 130–135 | >1.0 |

TABLE I-continued

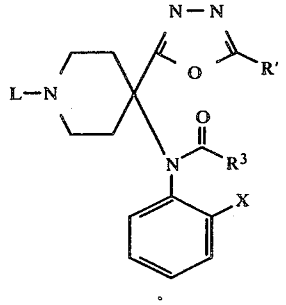

| Compound | L | R' | $R^3$ | X | M.P. (°C.) | $ED_{50}$ mg/kg mouse hot plate |
|---|---|---|---|---|---|---|
| 1-[2-(2-thienyl)ethyl]-4-(methoxymethyl-1,3,4-oxadiazolyl)-4-(N—phenylpropionamido)piperidinium chloride | 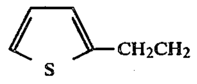 | $CH_3OCH_2$ | $CH_3CH_2$ | H | 121-126 | 0.0007 |
| 1-[2-(2-pyridinyl)ethyl]-4-methoxymethyl-1,3,4-oxadiazolyl)-4-(N—phenylpropionamido)piperidinium oxalate | 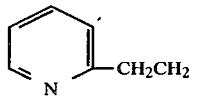 | $CH_3OCH_2$ | $CH_3CH_2$ | H | 157-158 | >1.0 |
| 1-(2-methylpropyl)-4-(methoxymethyl-1,3,4-oxadiazolyl)-4-(N—phenylpropionamido)piperidinium oxalate | $CH_3CHCH_3CH_2$ | $CH_3OCH_2$ | $CH_3CH_2$ | H | 214-215 | >1.0 |
| 1-(phenylethyl)-4-(methoxymethyl-1,3,4-oxadiazolyl)-4-(N—phenylpropionamido)piperidinium chloride | 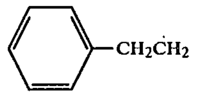 | $CH_3OCH_2$ | $CH_3CH_2$ | H | 115-120 | 0.0023 |
| 1-[2-(4-ethyl-4,5-dihydro-5-oxo-1H—tetrazol-1-yl)ethyl]-4-(methoxymethyl-1,3,4-oxadiazolyl)-4-(N—phenylpropionamido)piperidinium oxalate | 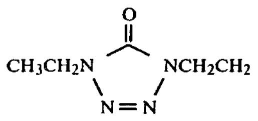 | $CH_3OCH_2$ | $CH_3CH_2$ | H | 153-154 | >5.0 |
| 1-[2-(4-methylthiazol-5-yl)ethyl]-4-(methoxymethyl-1,3,4-oxadiazolyl)-4-(N—phenylpropionamido)-piperidinium oxalate | 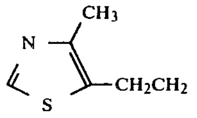 | $CH_3OCH_2$ | $CH_3CH_2$ | H | 227-228 | 0.718 |

TABLE I-continued

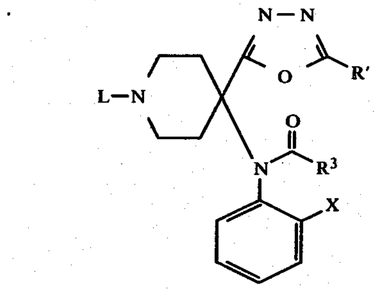

| Compound | L | R' | $R^3$ | X | M.P. (°C.) | $ED_{50}$ mg/kg mouse hot plate |
|---|---|---|---|---|---|---|
| 1-[2-(3,3-diethyl-2,4(1H,3H)—pyridinedion-1-yl)ethyl]-4-(methoxymethyl-1,3,4-oxadiazolyl)-4-(N—phenyl-propionamido)piperidinium oxalate | 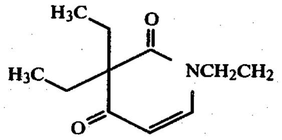 | $CH_3OCH_2$ | $CH_3CH_2$ | H | 160-161 | >1.0 |
| 1-(2-phenylethyl)-4-(methoxymethyl-1,3,4-oxadiazolyl)-4-(N—phenylmethoxyacetamido)piperidinium oxalate | 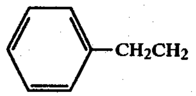 | $CH_3OCH_2$ | $CH_3OCH_2$ | H | 148-150 | 0.818 |
| 1-[2-(2-thienyl)ethyl]-4-(methoxymethyl-1,3,4-oxadiazolyl)-4-(N—phenylmethoxyacetamido)piperidinium oxalate | 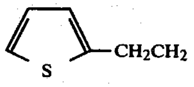 | $CH_3OCH_2$ | $CH_3OCH_2$ | H | 153-155 | >1.0 |
| 1-[2-(2-fluorophenyl)ethyl]-4-(methoxymethyl-1,3,4-oxadi-azolyl)-4-(N—phenylmethoxyacetamido)piperidinium oxalate | 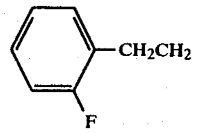 | $CH_3OCH_2$ | $CH_3OCH_2$ | H | 61-63 | 0.435 |
| 1-[2-(4-methylthiazol-5-yl)ethyl]-4-(methoxy-methyl-1,3,4-oxadiazolyl)-4-(N—phenylmethoxy-acetamido)piperidinium oxalate | 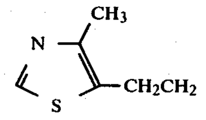 | $CH_3OCH_2$ | $CH_3OCH_2$ | H | 119-120 | >5.0 |
| 1-[2-(4-ethyl-4,5-dihydro-5-oxy-1H—tetrazol-1-yl)-4-(methoxymethyl-1,3,4-oxadiazolyl)-4-(N—phenylmethoxyacetamido)piperidinium oxalate | 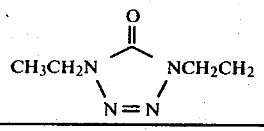 | $CH_3OCH_2$ | $CH_3OCH_2$ | H | 150-151 | >5.0 |

TABLE II

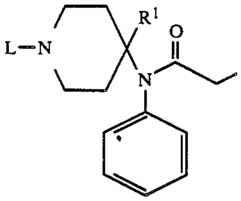

| Compound | L | $R^1$ | M.P. (°C.) | $ED_{50}$ mg/kg mouse hot plate |
|---|---|---|---|---|
| 1-(2-phenylethyl)-4-(1-methylimidazol-2-yl)-4-(N—phenylpropionamido)piperidinium oxalate | 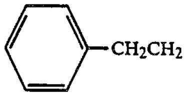 | 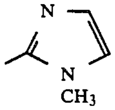 | 213-215 | 0.14 |
| 1-[2-(2-thienyl)ethyl]-4-(1-methylimidazol-2-yl)-4-(N—phenylpropionamido)piperidinium oxalate | 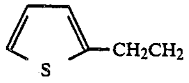 | 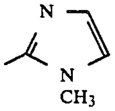 | 208-210 | 0.0096 |
| 1-[2-(1-pyrazolyl)ethyl]-4-(1-methylimidazol-2-yl)-4-(N—phenylpropionamido)piperidinium oxalate | 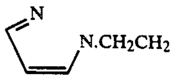 | 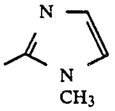 | 195-197 | >5.0 |
| 1-[2-(4-ethyl-4,5-dihydro-5-oxo-1H—tetrazol-1-yl)ethyl]-4-(1-methylimidazol-2-yl)-4-(N—phenylpropionamido)piperidinium oxalate | 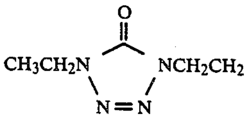 | 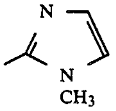 | 144-145 | >5.0 |
| 1-(2-phenylethyl)-4-(1-methyl-1,2,4-triazol-5-yl)-4-(N—phenylpropionamido)piperidinium oxalate | 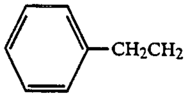 | 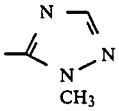 | 206-207 | 0.003 |
| 1-[2-(2-thienyl)ethyl]-4-(1-methyl-1,2,4-triazol-5-yl)-4-(N—phenylpropionamido)piperidinium oxalate | 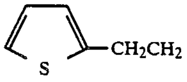 | 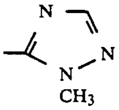 | 216-217 | 0.0023 |
| 1-[2-(4-methylthiazol-5-yl)ethyl]-4-(1-methyl-1,2,4-triazol-5-yl)-4-(N—phenylpropionamido)piperidinium oxalate | 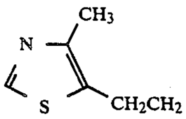 | 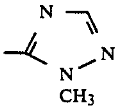 | 218-220 | 0.039 |
| 1-(2-thienyl)ethyl-4-(1-methyl-1H—tetrazol-5-yl)-4-(N—phenylpropionamido)piperidinium oxalate | 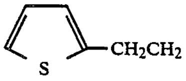 | 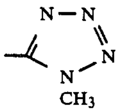 | 202-204 | 0.0097 |
| 1-[2-(1-pyrazolyl)ethyl]-4-(1-methyl-1H—tetrazol-5-yl)-4-(N—phenylpropionamido)piperidinium oxalate | 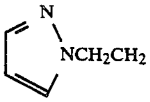 | 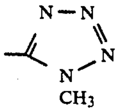 | 194-195 | 0.05 |
| 1-[2-(2-fluorophenyl)ethyl]-4-(1-methyl-1H—tetrazol-5-yl)-4-(N—phenylpropionamido)piperidinium oxalate | 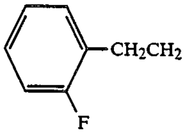 | 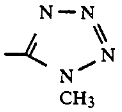 | 201-203 | 0.0048 |

TABLE II-continued

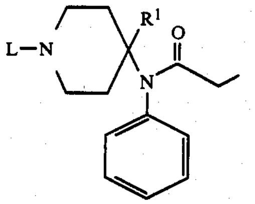

| Compound | L | $R^1$ | M.P. (°C.) | $ED_{50}$ mg/kg mouse hot plate |
|---|---|---|---|---|
| 1-[2-(1-pyrazolyl)ethyl]-4-(2-methyl-2H—tetrazol-5-yl)-4-(N—phenylpropionamido)piperidinium oxalate | 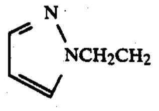 | 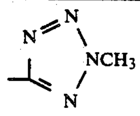 | 192–193 | >1.0 |
| 1-(4-ethyl-1,4-dihydro-5H—tetrazol-5-one-1-yl)ethyl-4-(2-methyl-2H—tetrazol-5-yl)-4-(N—phenylpropionamido)piperidinium oxalate | 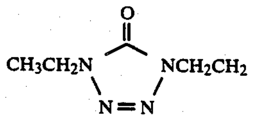 | 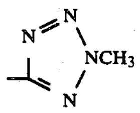 | 161–163 | >5.0 |
| 1-(2-thienyl)ethyl-4-(2-methyl-2H—tetrazol-5-yl)-4-(N—phenylpropionamido)piperidinium oxalate | 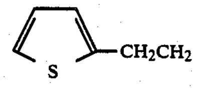 | 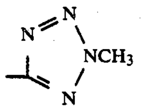 | 208–209 | 0.015 |
| 1-(2-phenylethyl)-4-(2-methyl-2H—tetrazol-5-yl)-4-(N—phenylpropionamido)piperidinium oxalate | 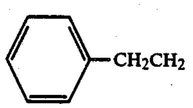 | 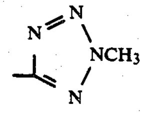 | 218–219 | 0.016 |
| 1-(2-methylbutyl)-4-(1-methyl-1,2,4-triazol-5-yl)-4-(N—phenylpropionamido)-piperidinium oxalate | $CH_3CH_2CHCH_3CH_2$ | 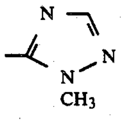 | 132–133 | 0.043 |
| 1-[2-(1-pyrazolyl)ethyl]-4-(1-methyl-1,2,4-triozol-5-yl)-4-(N—phenylpropionamido)-piperidinium oxalate | 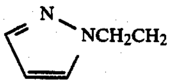 | 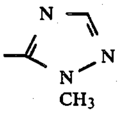 | 186–187 | >1.0 |
| 1-[2-(N—phthalimido)ethyl]-4-(1-methyl-1,2,4-triazol-5-yl)-4-(N—phenylpropionamido)-piperidinium oxalate | 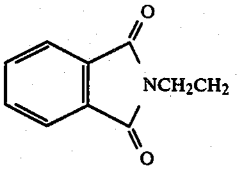 | 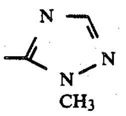 | 168–170 | >1.0 |
| 1-[2-(4-ethyl-4,5-dihydro-5-oxo-1H—tetrazol-1-yl)ethyl]-4-(1-methyl-1,2,4-triazol-5-yl)-4-(N—phenylpropionamido)-piperidinium oxalate | 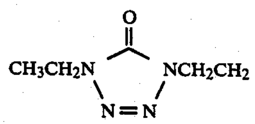 | 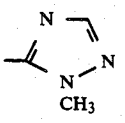 | 211–212 | >1.0 |
| 1-[2-(4-methylthiazol-5-yl)ethyl]-4-(1-methyl-1H—tetrazol-5-yl)-4-(N—phenylpropionamido)piperidinium oxalate | 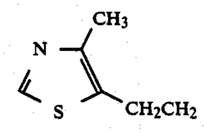 | 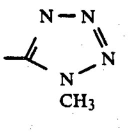 | 219–222 | 0.31 |
| 1-(2-methyl)butyl-4-(1-methyl-1H—tetrazol-5-yl)-4-(N—phenylpropionamido)piperidinium oxalate | $CH_3CH_2CHCH_3CH_2$ | 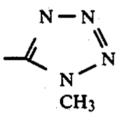 | 202–204 | 0.452 |

TABLE II-continued

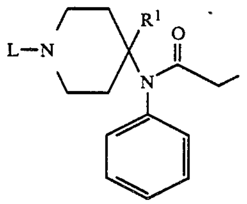

| Compound | L | $R^1$ | M.P. (°C.) | $ED_{50}$ mg/kg mouse hot plate |
|---|---|---|---|---|
| 1-(2-phenylethyl)-4-(1-methyl-1H—tetrazol-5-yl)-4-(N—phenylpropionamido)piperidinium oxalate | 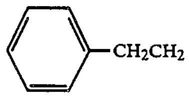 | 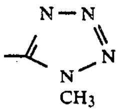 | 216–218 | 0.009 |

TABLE III

| | Compound | M.P. °C. | Analgesic Activity ($ED_{50}$)mg/kg Mice |
|---|---|---|---|
| 1. | 1-(2-phenylethyl)-4-(4-methyl-thiazol-2-yl)-4-[N—fluorophenyl)propionamido] piperidinium oxalate | 203.5–204.5 | 0.022 |
| 2. | 1-[2-(4-ethyl-4,5-dihydro-5-oxo-1H—tetra zol-1-yl)ethyl]-4-(4-methyl-thiazol-2-yl)-4-(N—phenylpropionamido) piperidinium oxalate | 154–55 | 0.264 |
| 3. | 1-[2-(4-ethyl-4,5-dihydro-5-oxo-1H—tetrazol-1-yl)ethyl]-4-(4-methyl-thiazol-2-yl)-4-[N—(2-fluorophenyl)propionamido] piperidinium oxalate | 144–46 | 0.179 |
| 4. | 1-[2-(1H—pyrazol-1-yl)ethyl]-4-(4-methyl-thiazol-2-yl)-4-(N—phenylpropionamido) piperidinium oxalate | 185–87 | 0.064 |
| 5. | 1-[2-1H—pyrazol-1-yl)ethyl]-4-(4-methyl-thiazol-2-yl)-4-[N—(2-fluorophenyl) propionamide] piperidinium oxalate | 185–87 | 0.047 |
| 6. | 1-[2-(2-thienyl)ethyl]-4-(4-methyl-thiazol-2-yl)-4-[N—(2-fluorophenyl) propionamido] piperidinium oxalate | 198–200 | 0.012 |
| 7. | 1-[2-(3-thienyl)ethyl]-4-(4-methyl-thiazol-2-yl)-4-[N—(2-fluorophenyl) propionamido] piperidinium oxalate | 202–204 | 0.0054 |
| 8. | 1-(2-phenylethyl)-4-(2-thiazolyl)-4-(N—phenyl propionamido) piperidinium oxalate | 193–94 | 0.0047 |
| 9. | 1-(2-phenylethyl)-4-(2-thiazolyl)-4-[N—(2-fluorophenyl)propionamido] piperidinium oxalate | 202–203 | 0.0034 |
| 10. | 1-[2-(4-ethyl-4,5-dihydro-5-oxo-1H—tetrazol-1-yl)ethyl]-4-(2-thiazolyl)-4-[N—phenylpropionamido) piperidinium oxalate | 169–70 | 0.212 |
| 11. | 1-[2-(4-ethyl-4,5-dihydro-5-oxo-1H—tetrazol-1-yl)ethyl]-4-(2-thiazolyl)-4-[N—(2-fluorophenyl)propionamido] piperidinium oxalate | 177–78 | 0.057 |
| 12. | 1-(2-phenylethyl)-4-(4,5-dimethyl-thiazol-2-yl)-4-(N—phenylpropionamido) piperidinium oxalate | 191–192 | >5.0 |
| 13. | 1-[2-(3-thienyl)ethyl]-4-(4,5-dimethyl-thiazol-2-yl)-4-(N—phenylpropionamido) piperidinium oxalate | 201–202 | 0.525 |
| 14. | 1-[2-(4-ethyl-4,5-dihydro-5-oxo-1H—tetrazol-1-yl)ethyl]-4-(4,5-dimethyl-thiazol-2-yl)-4-(N—phenylpropionamido) piperidinium oxalate | 194–95 | N/A |
| 15. | 1-(2-phenylethyl)-4-(4-methylthiazol-2-yl)-4-(N—phenylpropionamido) piperidinium oxalate | 204 | 0.072 |
| 16. | 1-[2-(2-thienyl)ethyl]-4-(4-methylthiazol-2-yl)-4-(N—phenylpropionamido) piperidinium oxalate | 181 | 0.01 |
| 17. | 1-[2-(3-thienyl)ethyl]-4-(4-methylthiazol-2-yl)-4-(N—phenylpropionamido) piperidinium oxalate | 202–204 | 0.0059 |
| 18. | 1-[2-(4-methylthiazol-5-yl)ethyl]-4-(4-methylthiazol-2-yl)-4-[N—(2-fluorophenyl) | 225 | 0.017 |

TABLE III-continued

| Compound | M.P. °C. | Analgesic Activity ($ED_{50}$)mg/kg Mice |
|---|---|---|
| propionamido] piperidinium oxalate | | |

It will be understood that the embodiments described herein are merely exemplary and that a person skilled in the art may make many variations and modifications without departing from the spirit and scope of the invention. All such modifications and variations are intended to be included within the scope of the invention as defined in the appended claims.

We claim:

1. A compound of the formula

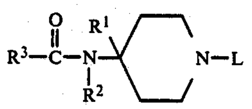

optically active isomeric forms thereof, or pharmaceutically acceptable acid addition salts thereof, in which formula: $R^1$ is an unsubstituted or substituted oxadiazolyl, tetrazolyl, imidazolyl, or thiazolyl wherein the substituents are selected from the group consisting of lower alkyl, lower alkoxy, lower alkoxy lower alkyl or combinations thereof; $R^2$ is unsubstituted or substituted phenyl in which the substituent is a halogen atom; $R^3$ is a lower alkyl or a lower alkoxy lower alkyl; and L is lower alkyl, lower alkoxy, thienyl lower alkyl, thiazolyl lower alkyl which is unsubstituted or substituted in the 4-position with a lower alkyl group; (4,5-di-hydro-5-oxo-1H-tetrazol-1-yl) lower alkyl which is unsubstituted or substituted in the 4-position with a lower alkyl; pyrazolyl lower alkyl, pyridinyl lower alkyl, oxo phenyl lower alkyl, N-pthalimido lower alkyl, 2,4-(1H,3H)-pyridinedionyl, disubstituted in the 3 position with lower alkyl; or an unsubstituted or substituted phenyl lower alkyl in which the substituents are selected from the group consisting of lower alkyl, lower alkoxy, halogen, halogenated lower alkyl, or combinations thereof.

2. A compound of the formula

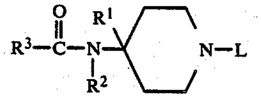

optically active isomeric forms thereof, or pharmaceutically acceptable acid addition salts thereof, in which formula: $R^1$ is 1,2,4-triazol-4-yl, 1-methylimidazol-2-yl, 1-methyl-1,2,4-triazol-5-yl, 1-methyl-1H-tetrazol-5-yl, 2-methyl-2H-tetrazol-5-yl, methyl or ethyl-1,3,4-oxadiazolyl, methoxymethyl-1,3,4-oxadiazolyl, and 4-methyl-thiazol-2-yl, 4,5-dimethyl-thiazol-2-yl, or thiazol-2-yl; $R^2$ is substituted or unsubstituted phenyl in which the substituent is a halogen atom; $R^3$ is a lower alkyl or a lower alkoxy lower alkyl; and L is lower alkyl, lower alkoxy, thienyl lower alkyl, thiazolyl lower alkyl which is unsubstituted or substituted in the 4-position with a lower alkyl; (4,5-di-hydro-5-oxo-1H-tetrazol-1-yl) lower alkyl which is unsubstituted or substituted in the 4-position with a lower alkyl; pyrazolyl lower alkyl, pyridinyl lower alkyl, oxo phenyl lower alkyl, N-pthalimido lower alkyl, 2,4-(1H,3H)-pyridinedionyl, disubstituted in the 3 position with lower alkyl; or unsubstituted and substituted phenyl lower alkyl in which the substituents are selected from the group consisting of lower alkyl, lower alkoxy, halogen, halogenated lower alkyl, or combinations thereof.

3. A compound according to claim 1 in which formula $R^1$ is 1,2,4-triazol-4-yl, 1-methylimidazol-2-yl, 1-methyl-1,2,4-triazol-5-yl, 1-methyl-1H-tetrazol-1-yl, 2-methyl-2H-tetrazol-5-yl, methyl or ethyl-1,3,4-oxadiazolyl, methoxymethyl-1,3,4-oxadiazolyl, 4-methyl-thiazol-2-yl, 4,5-dimethyl-thiazol-2-yl, or thiazol-2-yl.

4. A compound according to claim 1, which consists of 1-(2-phenylethyl)-4-(ethyl-1,3,4-oxadiazolyl)-4-(N-phenylpropionamido)piperidine or salt thereof.

5. A compound according to claim 1, which consists of 1-[2-(2-thienyl)ethyl]-4-(ethyl-1,3,4-oxadiazolyl)-4-(N-phenylpropionamido)piperidine or salt thereof.

6. A compound according to claim 1, which consist of 1-[2-(3-thienyl)ethyl]-4-(ethyl-1,3,4-oxadiazolyl)-4-(N-phenylpropionamido)piperidine or salt thereof.

7. A compound according to claim 1, which consist of 1-(2-phenylethyl)-4-(methyl-1,3,4-oxadiazolyl)-4-(N-phenylpropionamido)piperidine or salt thereof.

8. A compound according to claim 1, which consist of 1-[2-(4-ethyl-4,5-dihydro-5-oxy-1H-tetrazol-1-yl)ethyl]-4-(methyl-1,3,4-oxadiazolyl)-4-(N-phenylpropionamido)piperidine or salt thereof.

9. A compound according to claim 1, which consist of phenylethyl)-4-(propyl-1,3,4-oxadiazolyl)-4-(N-phenylpropionamido)piperidine or salt thereof.

10. A compound according to claim 1, which consist of 1-[2-(2-thienyl)ethyl]-4-(propyl-1,3,4-oxadiazolyl)-4-(N-phenylpropionamido)piperidine or salt thereof.

11. A compound according to claim 1, which consist of 1-(2-phenylethyl)-4-(butyl-1,3,4-oxadiazolyl)-4-(N-phenylpropionamido)piperidine or salt thereof.

12. A compound according to claim 1, which consist of 1-[2-(2-thienyl)ethyl]-4-(methoxymethyl-1,3,4-oxadiazolyl)-4-(N-phenyl-propionamido)piperidine or salt thereof.

13. A compound according to claim 1, which consist of 1-(phenylethyl)-4-(methoxymethyl-1,3,4-oxadiazolyl)-4-(N-phenyllpropionamido)piperidine or salt thereof.

14. A compound according to claim 1, which consist of 1-[2-(4-methylthiazol-5-yl)ethyl]-4-(methoxymethyl-1,3,4-oxadiazolyl)-4-(N-phenylpropionamido)piperidine or salt thereof.

15. A compound according to claim 1, which consist of 1-(2-phenylethyl)-4-(1-methyl-1,2,4-triazol-5-yl)-4-(N-phenylpropionamido)piperidine or salt thereof.

16. A compound according to claim 1, which consist of 1-[2-(4-methylthiazol-5-yl)ethyl]-4-(methyl-1,2,4-triazol-5-yl)-4-(N-phenylpropionamido)piperidine or salt thereof.

17. A compound according to claim 1, which consist of 1-[2-(4-methylthiazol-5-yl)ethyl]-4-(1-methyl-1H-tetrazol-5-yl)-4-(N-phenylpropionamido)piperidine or salt thereof.

18. A compound according to claim 1, which consist of 1-[2-(2-fluorophenyl)ethyl]-4-(1-methyl-1H-tetrazol- 5-yl)-4-(N-phenylpropionamido)piperidine or salt thereof.

19. A compound according to claim 1, which consist of 1-benzyl-4-(4-methyl-thiazol-2-yl)-4-(N-phenylpropionamido)piperidine or salt thereof.

20. A narcotic agonist or analgesic composition comprising a non-toxic pharmaceutically acceptable carrier and therapeutically effective amount of a compound of the formula

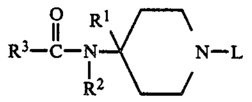

optically active isomeric forms thereof, or pharmaceutically acceptable acid addition salts thereof, in which formula: $R^1$ is an unsubstituted or substituted oxadiazolyl, tetrazolyl, imidazolyl, or thiazolyl, wherein the substituents are selected from lower alkyl, lower alkoxy, lower alkoxy lower alkyl, or combinations thereof; $R^2$ is unsubsttuted or substituted phenyl in which the substituent is a halogen atom; $R^3$ is a lower alkyl or a lower alkoxy lower alkyl; and L is lower alkyl, lower alkoxy, phenyl lower alkyl, thienyl lower alkyl, thiazolyl lower alkyl which is unsubstituted or substituted in the 4-position with a methyl group; (4,5-dihydro-5-oxo-1H-tetrazol-1-yl) lower alkyl which is unsubstituted or substituted in the 4-position with lower alkyl; pyrazolyl lower alkyl, pyridinyl lower alkyl, oxo phenyl lower alkyl, N-pthalimido lower alkyl, 2,4-(1H,3H)-pyridinyl, disubstituted in the 3 position with lower alkyl; or an unsubstituted or substituted phenyl lower alkyl in which the substituents are selected from the group consisting of lower alkyl, lower alkoxy, halogen, halogenated lower alkyl, or combinations thereof.

21. A narcotic agonist or analgesic composition according to claim 20, comprising a non-toxic pharmaceutically acceptable carrier and therapeutically effective amount of a compound of the formula

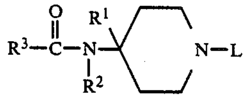

optically active isomeric forms thereof, or pharmaceutically acceptable acid addition salts thereof, in which formula: $R^1$ is 1,2,4-triazol-4-yl, 1-methyl-imidazol-2-yl, 1-methyl-1,2,4-triazol-5-yl, 1-methyl-1H-tetrazol-5-yl, 2-methyl-2H-tetrazol-5-yl, methyl or ethyl-1,3,4-oxadiazolyl, methoxymethyl-1,3,4-oxadiazolyl, 4-methyl-thiazol-2-yl, 4,5-dimethyl-thiazol-2-yl, or thiazol-2-yl; $R^2$ is unsubstituted or substituted phenyl in which the substituent is a halogen atom; $R^3$ is a lower alkyl or a lower alkoxy lower alkyl; and L is lower alkyl, lower alkoxy, thienyl lower alkyl, thiazolyl lower alkyl which is unsubstituted or substituted in the 4-position with a lower alkyl; (4,5-di-hydro-5-oxo-1H-tetrazol-1-yl) lower alkyl which is unsubstituted or substituted in the 4-position with a lower alkyl; pyrazolyl lower alkyl, pyridinyl lower alkyl, oxo phenyl lower alkyl, N-pthalimido lower alkyl, 2,4-(1H,3H)-pyridinedionyl, disubstituted in the 3 position with lower alkyl; and unsubstituted and substituted phenyl lower alkyl in which the substituents are selected from the group consisting of lower alkyl, lower alkoxy, halogen, halogenated lower alkyl, or combinations thereof.

22. A composition according to claim 20 in which formula $R^1$ is 1,2,4-triazol-4-yl, 1-methylimidazol-2-yl, 1-methyl-1,2,4-triazol-5-yl, 1-methyl-1H-tetrazol-5-yl, 2-methyl-2H-tetrazol-5-yl, ethyl or methyl-1,3,4-oxadiazolyl, methoxymethyl-1,3,4-oxadiazolyl, 4-methylthiazol-2-yl, 4,5-dimethyl-thiazol-2-yl, or thiazol-2-yl.

23. A composition according to claim 20, which consist of 1-(2-phenylethyl)-4-(ethyl-1,3,4-oxadiazolyl)-4-(N-phenyl-propionamido)piperidine or salt thereof.

24. A composition according to claim 20, which consist of 1-[2-(2-thienyl)ethyl]-4-(ethyl-1,3,4-oxadiazolyl)-4-(N-phenylpropionamido)piperidine or salt thereof.

25. A composition according to claim 20, which consist of 1-[2-(3-thienyl)ethyl]-4-(ethyl-1,3,4-oxadiazolyl)-4-(N-phenylpropionamido)piperidine or salt thereof.

26. A composition according to claim 20, which consist of 1-(2-phenylethyl)-4-(methyl-1,3,4-oxadiazolyl)-4-(N-phenyl-propionamido)piperidine or salt thereof.

27. A composition according to claim 20, which consist of 1-[2-(4-ethyl-4,5-dihydro-5-oxy-1H-tetrazol-1-yl)ethyl]-4-(methyl-1,3,4-oxadiazolyl)-4-(N-phenylpropionamido)piperidine or salt thereof.

28. A composition according to claim 20, which consist of 1-(2-phenylethyl)-4-(propyl-1,3,4-oxadiazolyl)-4-(N-phenylpropionamido)piperidine or salt thereof.

29. A composition according to claim 20, which consist of 1-[2-(2-thienyl)ethyl]-4-(propyl-1,3,4-oxadiazolyl)-4-(N-phenylpropionamido)piperidine or salt thereof.

30. A composition according to claim 20, which consist of 1-(2-phenylethyl)-4-(butyl-1,3,4-oxadiazolyl)-4-(N-phenylpropionamido)piperidine or salt thereof.

31. A composition according to claim 20, which consist of 1-[2-(2-thienyl)ethyl]-4-(methoxymethyl-1,3,4-oxadiazolyl)-4-(N-phenylpropionamido)piperidine or salt thereof.

32. A composition according to claim 20, which consist of 1-(phenylethyl)-4-(methoxymethyl-1,3,4-oxadiazolyl)-4-(N-phenylpropionamido)piperidine or salt thereof.

33. A composition according to claim 20, which consist of 1-[2-(4-methylthiazol-5-yl)ethyl]-4-(methoxymethyl-1,3,4-oxadiazolyl)-4-(N-phenylpropionamido)-piperidine or salt thereof.

34. A composition according to claim 20, which consist of 1-(2-phenylethyl)-4-(1-methyl-1,2,4-triazol-5-yl)-4-(N-phenylpropionamido)piperidine or salt thereof.

35. A composition according to claim 20, which consist of 1-[2-(4-methylthiazol-5-yl)ethyl]-4-(methyl-1,2,4-triazol-5-yl)-4-(N-phenylpropionamido)piperidine or salt thereof.

36. A composition according to claim 20, which consist of 1-[2-(4-methylthiazol-5-yl)ethyl]-4-(1-methyl-1H-tetrazol-5-yl)-4-(N-phenylpropionamido)piperidine or salt thereof.

37. A composition according to claim 20, which consist of 1-[2-(2-fluorophenyl)ethyl]-4-(1-methyl-1H-tetrazol-5-yl)-4-(N-phenylpropionamido)piperidine or salt thereof.

38. A composition according to claim 20, which consist of 1-benzyl-4-(4-methyl-thiazol-2-yl)-4-(N-phenyl-propionamido)piperidine or salt thereof.

39. A method for providing analgesia in a mammal, comprising administering to such mammal an analgesically effective amount of a compound of the formula

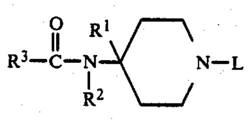

optically isomeric forms thereof, or pharmaceutically acceptable acid addition salts thereof, in which formula: $R^1$ is an unsubstituted or substituted oxadiazolyl, tetrazolyl, imidazolyl, or thiazolyl wherein the substituents are selected from the group consisting of lower alkyl, lower alkoxy, lower alkoxy lower alkyl or combinations thereof; $R^2$ is unsubstituted or substituted phenyl in which the substituent is a halogen atom; $R^3$ is a lower alkyl or a lower alkoxy lower alkyl; and L is lower alkyl, lower alkoxy, phenyl lower alkyl, thienyl lower alkyl, thiazolyl lower alkyl which is unsubstituted or substituted in the 4-position with a lower alkyl; (4,5-dihydro-5-oxo-1H-tetrazol-1-yl) lower alkyl which is unsubstituted or substituted in the 4-position with a lower alkyl; pyrazolyl lower alkyl, pyridinyl lower alkyl, oxo phenyl lower alkyl, N-pthalimido lower alkyl, 2,4-(1H,3H)pyridinedionyl, which is disubstituted in the 3 position with lower alkyl, or unsubstituted or substituted phenyl lower alkyl in which the substituents are selected from the group consisting of lower alkyl, lower alkoxy, halogen, halogenated lower alkyl, or combinations thereof.

40. A method for providing analgesia in a mammal according to claim 39, comprising administering to such mammal an analgesically effective amount of a compound of the formula

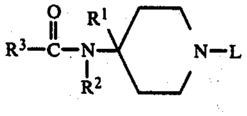

optically isomeric forms thereof, or pharmaceutically acceptable acid addition salts thereof, in which formula: $R^1$ is 1,2,4-triazol-4-yl, 1-methylimidazol-2-yl, 1-methyl-1,2,4-triazol-5-yl, 1-methyl-1H-tetrazol-5-yl, 2-methyl-2H-tetrazol-5-yl, methyl or ethyl-1,3,4-oxadiazolyl, methoxyethoxy-1,3,4-oxadiazolyl, 4-methyl-thiazol-2-yl, 4,5-dimethyl-thiazol-2-yl, or thiazol-2-yl; $R^2$ is unsubstituted or substituted phenyl in which the substituent is a halogen atom; $R^3$ is a lower alkyl or a lower alkoxy lower alkyl; and L is lower alkyl, lower alkoxy, thienyl lower alkyl, thiazolyl lower alkyl wich is unsubstituted or substituted in the 4-position with a lower alkyl; (4,5-di-hydro-5-oxo-1H-tetrazol-1-yl) lower alkyl which is unsubstituted or substituted in the 4-position with a lower alkyl; pyrazolyl lower alkyl,pyridinyl lower alkyl, oxo phenyl lower alkyl, N-phthalimido lower alkyl, 2,4-(1H,3H)-pyridinedionyl, which is disubstituted in the 3 position with lower alkyl, or unsubstituted or substituted phenyl lower alkyl in which the substituents are selected from the group consisting of lower alkyl, lower alkoxy, halogen, halogenated lower alkyl, or combinations thereof.

41. A method according to claim 39 in which formula $R^1$ is 1,2,4-triazol-4-yl, 1-methylimidazol-2-yl, 1-methyl-1,2,4-triazol-5-yl, 1-methyl-1H-tetrazol-5-yl, 2-methyl-2H-tetrazol-5-yl, ethyl or methyl-1,3,4-oxadiazolyl, methoxymethyl-1,3,4-oxadiazolyl, 4-methylthiazol-2-yl, 4,5-dimethyl-thiazol-2-yl, or thiazol-2-yl.

42. A method according to claim 39, comprising administering to such mammal an analgesically effective amount of 1-(2-phenylethyl)-4-(ethyl-1,3,4-oxadiazolyl)-4-(N-phenylpropionamido)piperidine or salt thereof.

43. A method according to claim 39, comprising administering to such mammal an analgesically effective amount of 1-[2-(2-thienyl)ethyl]-4-(ethyl-1,3,4-oxadiazolyl)-4-(N-phenylpropionamido)piperidine or salt thereof.

44. A method according to claim 39, comprising administering to such mammal an analgesically effective amount of 1-[2-(3-thienyl)ethyl]-4-(ethyl-1,3,4-oxadiazolyl)-4-(N-phenylpropionamido)piperidine or salt thereof.

45. A method according to claim 39, comprising administering to such mammal an analgesically effective amount of 1-(2-phenylethyl)-4-(methyl-1,3,4-oxadiazolyl)-4-(N-phenylpropionamido)piperidine or salt thereof.

46. A method according to claim 39, comprising administering to such mammal an analgesically effective amount of 1-[2-(4-ethyl-4,5-dihydro-5-oxy-1H-tetrazol-1-yl)ethyl]-4-(methyl-1,3,4-oxadiazolyl)-4-(N-phenylpropionamido)piperidine or salt thereof.

47. A method according to claim 39, comprising administering to such mammal an analgesically effective amount of 1-(2-phenylethyl)-4-(propyl-1,3,4-oxadiazolyl)-4-(N-phenylpropionamido)piperidine or salt thereof.

48. A method according to claim 39, comprising administering to such mammal an analgesically effective amount of 1-[2-(2-thienyl)ethyl]-4-(propyl-1,3,4-oxadiazolyl)-4-(N-phenylpropionamido)piperidine or salt thereof.

49. A method according to claim 39, comprising administering to such mammal an analgesically effective amount of 1-(2-phenylethyl)-4-(butyl-1,3,4-oxadiazolyl)-4-(N-phenylpropionamido)piperidine or salt thereof.

50. A method according to claim 39, comprising administering to such mammal an analgesically effective amount of 1-[2-(2-thienyl)ethyl]-4-(methoxymethyl-1,3,4-oxadiazolyl)-4-(N-phenylpropionamido)piperidine or salt thereof.

51. A method according to claim 39, comprising administering to such mammal an analgesically effective amount of 1-(phenylethyl)-4-(methoxymethyl-1,3,4-oxadiazolyl)-4-(N-phenylpropionamido)piperidine or salt thereof.

52. A method according to claim 39, comprising administering to such mammal an analgesically effective amount of 1-[2-(4-methylthiazol-5-yl)ethyl]-4-(methoxymethyl-1,3,4-oxadiazolyl)-4-(N-phenylpropionamido)piperidine or salt thereof.

53. A method according to claim 39, comprising administering to such mammal an analgesically effective amount of 1-(2-phenylethyl)-4-(1-methyl-1,2,4-triazol-5-yl)-4-(N-phenylpropionamido)piperidine or salt thereof.

54. A method according to claim 39, comprising adminitering to such mammal an analgesically effective amount of 1-[2-(4-methylthiazol-5-yl)ethyl]-4-(methyl-1,2,4-triazol-5-yl)-4-(N-phenylpropionamido)piperidine or salt thereof.

55. A method according to claim 39, comprising administering to such mammal an analgesically effective amount of 1-[2-(4-methylthiazol-5-yl)ethyl]-4-(1- methyl-1H-tetrazol-5-yl)-4-(N-phenylpropionamido)-piperidine or salt thereof.

56. A method according to claim 39, comprising administering to such mammal an analgesically effective amount of 1-[2-(2-fluorophenyl)ethyl]-4-(1-methyl-1H-tetrazol-5-yl)-4-(N-phenylpropionamido)piperidine or salt thereof.

57. A method according to claim 39, comprising administering to such mammal an analgesically effective amount of 1-benzyl-4-(4-methyl-thiazol-2-yl)-4-(N-phenylpropionamido)piperidine or salt thereof.

* * * * *

UNITED STATES PATENT AND TRADEMARK OFFICE

CERTIFICATE OF CORRECTION

PATENT NO. : 4,791,120

DATED : December 13, 1988

INVENTOR(S) : B. Lin et al

It is certified that error appears in the above-identified patent and that said Letters Patent is hereby corrected as shown below:

Column 49, line 24, Claim 1, after "tetrazolyl", insert --triazolyl, --.

Column 51, line 29, Claim 20, after "tetrazol-1-yl)", insert --triazolyl,--.

Column 53, lines 9 and 10, Claim 39, after "tetrazolyl", insert --triazolyl, --.

Signed and Sealed this

Fourth Day of September, 1990

Attest:

HARRY F. MANBECK, JR.

*Attesting Officer* *Commissioner of Patents and Trademarks*